(12) United States Patent
Schabert et al.

(10) Patent No.: US 6,660,494 B2
(45) Date of Patent: Dec. 9, 2003

(54) DETECTION OF MICROBIAL METABOLITES

(75) Inventors: Günter Schabert, Goldach (CH); Lawrence Restaino, Chicago, IL (US); Elon W. Frampton, DeKalb, IL (US)

(73) Assignee: Biosynth AG (CH)

( * ) Notice: Subject to any disclaimer, the term of this patent is extended or adjusted under 35 U.S.C. 154(b) by 61 days.

(21) Appl. No.: 10/021,271

(22) Filed: Dec. 19, 2001

(65) Prior Publication Data

US 2002/0151725 A1 Oct. 17, 2002

(30) Foreign Application Priority Data

Dec. 27, 2000  (EP) ............................................. 00128552

(51) Int. Cl.⁷ .............................. C12Q 1/04; C12Q 1/02; C12Q 1/42; C12Q 1/18; G01N 33/53
(52) U.S. Cl. .............................. 435/34; 435/29; 435/18; 435/21; 435/32; 435/252.31; 435/253.3; 435/975; 548/414
(58) Field of Search .............................. 435/34, 29, 18, 435/32, 252.31, 253.3, 975; 548/414

(56) References Cited

U.S. PATENT DOCUMENTS

| 4,082,781 A | 4/1978 | Gal ............................ 260/403 |
| 6,416,970 B1 * | 7/2002 | Schabert et al. ............... 435/34 |
| 2002/0151725 A1 * | 10/2002 | Schabert et al. ............. 548/414 |

FOREIGN PATENT DOCUMENTS

| WO | WO 98/38332 | 9/1998 |
| WO | WO 99/50438 | 10/1999 |

OTHER PUBLICATIONS

Kurioka et al., Phospholipase C assay using p–nitrophenylphosphorylcholine together with sorbitol and its application to studying the metal and detergent requirement of the enzyme, XP–001002863—Biochemistry . . . , vol. 75, 1976, pp. 281–289.

(List continued on next page.)

Primary Examiner—Louise N. Leary
(74) Attorney, Agent, or Firm—Blank Rome LLP

(57) ABSTRACT

Chromogenic 3-Indoxyl choline phosphate compounds of formula (I):

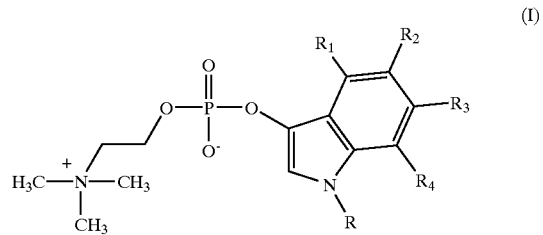

Figure 1:
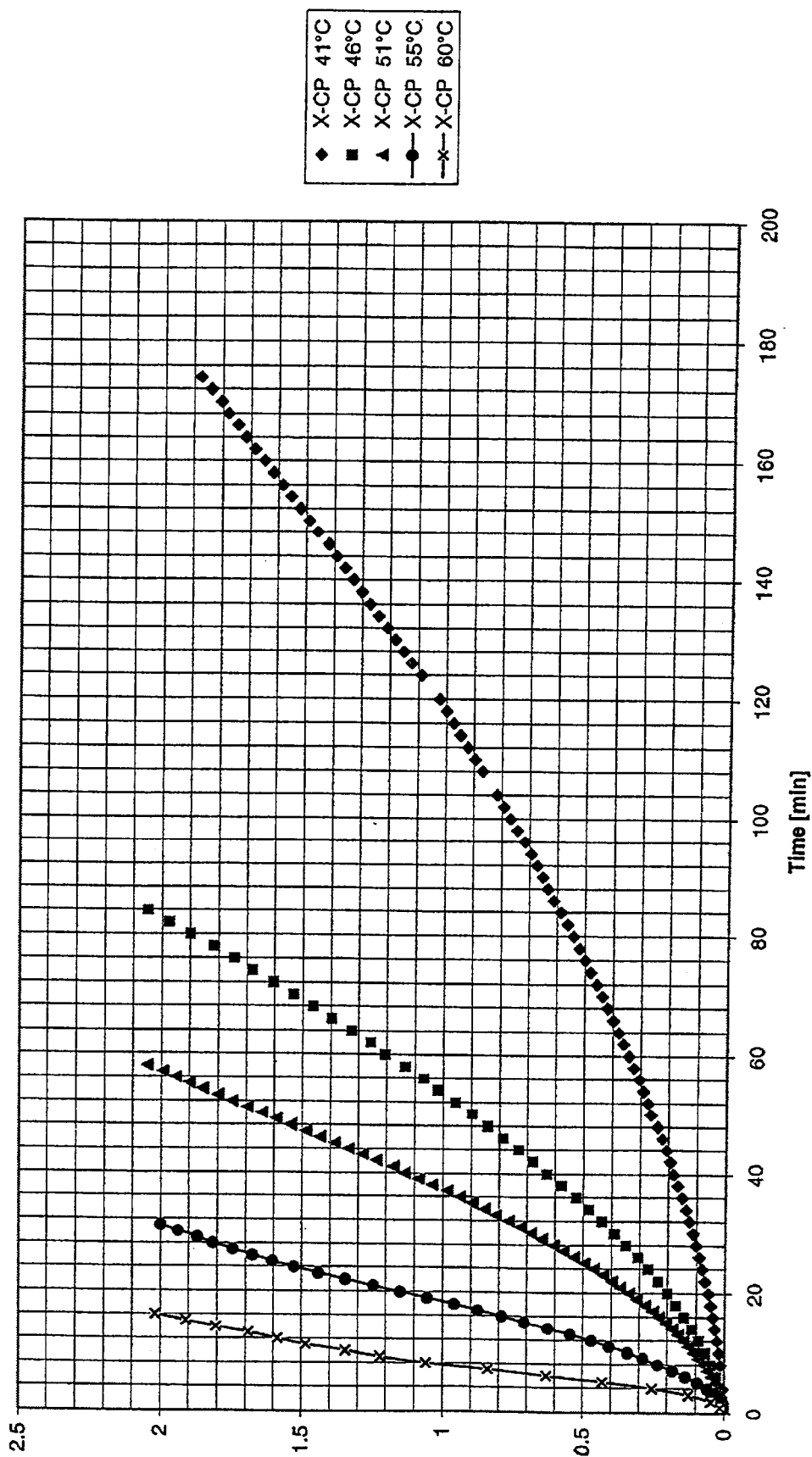

wherein R is selected from the group consisting of hydrogen and $C_{1-4}$ alkyl, such as methyl, ethyl, propyl and butyl while $R^1$, $R^2$, $R^3$, and $R^4$ are independently selected from the group consisting of hydrogen, halogen, cyano, nitro, carboxy, amino, amino substituted with one or two $C_{1-4}$ alkyl groups, aminomethyl, hydroxy, $C_{1-4}$ alkoxy, carboxyalkyl, and sulphonyl. These compounds are capable of being cleaved by lecithinase C leading to products which are calorimetrically detectable. The invention provides safe and sensitive detection of potentially pathogenic bacterial activity of such microbes as *Clostridium perfringens, Bacillus cereus, Bacillus anthracis, Pseudomonas aeruginosa, Listeria monocytogenes, Heliobacter pylori, Legionella pneumophila,* and others in material which may contain such activity typically including physiological samples, goods for consumption, such as food and beverages, and any other potentially infected objects or articles.

40 Claims, 7 Drawing Sheets

OTHER PUBLICATIONS

Songer, Bacterial Phospholipases and their role in virulence, Trends in Microbiology, vol. 5, No. 4, 1997, pp. 156–161.

Guttmann et al., Phenotypic and genotypic comparisons of 23 strains from the *Bacillus cereus* complex for a selection of known and putative *B. thuringiensis* virulence factors, FEMS Microbiology Letters, vol. 188, 2000, pp. 7–13.

Baine, A Phospholipase C from the Dallas IE Strain of *Legionella pneumophila* Serogroup 5: Purification and Characterization of Conditions for Optimal Activity with an Artificial Substrate, Journal of General Microbiology, vol. 134, 1988, pp. 489–498.

Coffey et al., Influence of Environmental Parameters on Phosphatidylcholine Phospholipase C Production in *Listeria monocytogenes*: a Convenient Method to Differentiate *L. monocytogenes* from Other Listeria Species, Applied and Environmental Microbiology, vol. 62, No. 4, 1996, pp. 1252–1256.

Birch et al., Evidence of Multiple Extracellular Phospholipase Activities of *Aspergillus fumigatus*, Infection and Immunity, vol. 64, No. 3, 1996, pp. 751–755.

Krug et al., Phospholipase C from *Clostridium perfringens*: Preparation and Characterization of Homogeneous Enzyme, Archives of Biochemistry and Biophysics, vol. 231, No. 2, 1984, p. 400–410.

Kurioka et al., Phospholipase C Assay Using p–Nitrophenylphosphoryl–choline Together with Sorbitol and Its Application to Studying the Metal and Detergent Requirement of the Enzyme, Academic Press, Inc. 1976, pp. 281–289.

Kurioka, Synthesis of p–Nitrophenylphosphorylcholine and the Hydrolysis with Phospholipase C*, The Journal of Biochemistry, vol. 63, No. 5, 1968, pp. 678–680.

Chrisope et al., Lecithin Agar for Detection of Microbial Phospholipases[1], Applied and Environmental Microbiology, vol. 31, No. 5, 1976, p. 784–786.

Carlson et al., Genotypic Diversity among *Bacillus cereus* and *Bacillus thuringiensis* Strains, Applied and Environmental Microbiology, vol. 60, No. 6, 1994, p. 1719–1725.

El–Sayed, Sensitivity of phospholipase C (*Bacillus cereus*) activity to phosphatidylcholine structural modifications, Biochimica et Biophysica Acia, vol. 837, 1985, pp. 325–335.

Chesebro et al., Affinity Labeling of a Phosphorylcholine Binding Mouse Myeloma Protein, Biochemistry, vol. 11, No. 5, 1972, pp. 766–771.

Krug et al., [23] Assay for Phospholipase C, Methods in Enzymology, vol. 72, pp. 347–351.

Weitkamp et al., Identification and Characterization of *Helicobactor pylori* Phospholipase C Activity, Zbl. Bakt. vol. 280, 1993, pp. 11–27.

* cited by examiner

DETECTION OF MICROBIAL METABOLITES

CROSS REFERENCE TO RELATED APPLICATION

This application is related to pending application Ser. No. 09/646,528 filed Sep. 19, 2000 in the name of Günter Schabert, applicant herein and assigned to Biosynth AG, assignee of the present application.

FIELD OF THE INVENTION

The present invention relates to novel compounds and substrates having utility for detection of microbial metabolites, i.e. substances secreted or otherwise produced by such microorganisms, by color formation upon contact with such metabolites, as well as to methods of producing such compounds and substrates and of using them for detection and identification of various microorganisms including bacteria.

PRIOR ART

Phospholipase C enzymes are found in a variety of microbes. These enzymes have been associated with the pathogenicity of the microbes to its host.

More specifically, it is known that an enzyme named "phosphatidylcholine-specific phospholipase C (also known as phosphatidylcholine cholinephosphohydrolase, or lecithinase C, termed PC-PLC herein for short; enzyme classification EC 3.1.4.3) can be found in a variety of microbes including *Clostridium perfringens, Clostridium novyi, Bacillus cereus, Bacillus thuringiensis, Pseudomonas aeruginosa* and *Staphylococcus aureus* (cf. J. G. Songer; Trends in Microbiology 5 (1997), 156) as well as *Bacillus anthracis* (cf D. M. Guttmann, D. J. Ellar, FEMS Microbiology Letters 188 (2000) 7), *Helicobacter pylori* (cf. J.-H. Weitkamp et al.; Zentralblatt für Bakteriologie 280 (1993), 11), *Legionella pneumophila* (cf. W. B. Baine; Journal of General Microbiology 134 (1988), 489), and *Listeria monocytogenes* (cf. A. Coffey et al.; Applied and Environmental Microbiology 62 (1996), 1252). Furthermore, PC-PLC has been found in yeasts, e.g. *Candida albicans,* and in molds, e.g. *Aspergillus fumigatus* (cf. M. Birch et al.; Infect. Immun. 64 (1996), 751).

Several procedures for assay of PC-PLC have been developed. Some of the more recent assays were reviewed by E. L. Krug and C. Kent (cf. Methods in Enzymology 72 (1981), 347). The most commonly used procedures detect choline phosphate produced by the phospholipase C reaction on the natural substrate phosphatidylcholine. For other methods special equipment is needed. All these methods allow only measurement of the total amount of enzyme present in a sample at a certain moment and therefore are discontinuous assay methods. Additionally, all these procedures are clearly not suitable for the direct detection of microbes secreting PC-PLCs.

In 1976, Kurioka et al. (cf. S. Kurioka, M. Matsuda; Analytical Biochemistry 75 (1976), 281) have reported a continuous spectrophotometric assay for PC-PLC using a substrate containing 4-Nitrophenyl choline phosphate (p-Nitrophenylphosphorylcholine). Kurioka first synthesized this compound in 1968 (cf. S. Kurioka; Journal of Biochemistry 63 (1968), 678).

However, this substrate has several disadvantages. The specific activity of the enzyme towards this substrate is extremely low. Only after the addition of sorbitol or glycerol in high concentrations (up to 60%) an assay of PC-PLC with reasonable, yet still low cleavage rates could be developed. Thus, as already stated by Krug and Kent, this procedure is only suitable for investigations with pure enzyme preparations. This means that this substrate is less suitable for direct detection of microbes or microbial secretes containing PC-PLCs.

Furthermore, this substrate cannot be used for plating media since the 4-nitrophenolate liberated upon enzymatic cleavage is water-soluble and thus would migrate into the medium. Additionally, the yellow color of 4-Nitrophenolate may interfere with the background in biological samples like body fluids or culture media.

To sum up, prior art assay methods are unspecific, not flexible and do not allow continuous measurement of actual PC-PLC concentrations in a sample.

Prior art methods for detection and identification of bacteria producing PC-PLC use freshly prepared egg yolk agar. Egg yolk contains a variety of phosphatides; the main constituents are phosphatidylcholine, phosphatidylethanolamine and inositol phosphatides. Phosphatidylcholine is cleaved by PC-PLC to form choline phosphate and water-insoluble diglycerides, the latter giving an opaque zone around the bacterial colonies producing PC-PLC on egg yolk agar.

These methods were improved by the use of Lecithin agar (cf. G. L. Chrisope et al.; Applied and Environmental Microbiology 31 (1976), 784) containing crude soybean lecithin. Bacteria secreting PC-PLC showed turbid halos around the colonies indicating the presence of the enzyme. The average time to produce a reaction of moderate degree was about two to three days. This detection method lacks specificity because other phospholipases, e.g. phospholipase A or phosphatidylinositol-specific phospholipase C (PI-PLC) may act on other components of lecithin producing opalescent zones around the colony, too. Furthermore, training is required to correctly screen the plates for such zones. Generally, these prior art methods are unspecific, laborious and time consuming and, hence, expensive.

Moreover, prior art detecting systems generally fail to distinguish between different bacteria. For example, there is no simple plating medium to discriminate between *Bacillus cereus* and *Bacillus thuringiensis,* in particular since data show that *Bacillus cereus* and *Bacillus thuringiensis* should be regarded as one species (cf. C. R. Carlson, Applied and Environmental Microbiology 60 (1994), 1719) where horizontal transfer of plasmid genome occurs.

OBJECTS AND SUMMARY OF THE INVENTION

Accordingly it is a primary object of the present invention to provide novel chromogenic compounds for easy and convenient detection of PC-PLC, which avoid the disadvantages of prior art.

It is another main object of the present invention to provide novel chromogenic substrates and methods for detection and/or identification of microorganisms producing PC-PLC by means of conventional spectrophotometric and/or histochemical assay methods including use in broth, and notably in plating media, and which substrates are substantially free from the disadvantages of prior art substrates or methods.

It is a further object of the present invention to provide means for detecting and/or identifying various pathological bacteria, such as *Clostridium perfringens, Pseudomonas aeruginosa, Helicobacter pylori, Legionella pneumophila, Bacillus cereus, Bacillus anthracis, Listeria monocytogenes* and others.

Yet another object of the present invention is a method to discriminate *Bacillus cereus* from *Bacillus thuringiensis.*

The above and further objects and advantages apparent from the present disclosure will be achieved by means of certain novel chromogenic compounds of formula (I):

(I)

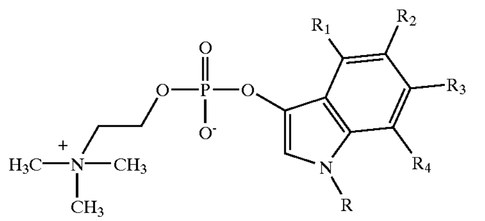

in which R is selected from the group consisting of hydrogen and $C_{1-4}$ alkyl, such as methyl, ethyl, and all possible isomers of propyl and butyl, while $R^1$, $R^2$, $R^3$, and $R^4$ are radicals independently selected from the group consisting of hydrogen, halogen (e.g. fluorine, chlorine, bromine and iodine), cyano, nitro, carboxy, amino, amino substituted with one or two $C_{1-4}$ alkylgroups, aminomethyl, hydroxy, $C_{1-4}$ alkoxy, carboxyalkyl, and sulphonyl.

The term "chromogenic" as used herein with reference to compounds according to the invention is intended to indicate the capacity of such compounds to become colored, i.e. visibly or calorimetrically detectable upon interaction with bacteria and, specifically, upon interaction with PC-PLC.

The terms "detection" or "detecting" are intended herein to include detection methods and assay techniques, as well as substances or substrates for use in such methods or techniques.

As will be apparent to those experienced in the art, most preferred compounds within the scope of formula (I) above are those which will yield deeply colored indigo dyes when used as substrates for detecting PC-PLCs, and which, preferably, are easily available and generally suitable for histochemical uses. Typical examples of preferred formula (I) compounds will be given herein below.

While no limitation is intended by such explanation, effectiveness of compounds of formula (I) as substrates for detection of PC-PLC enzymes is believed to reside in the fact that cleavage of a compound according to the invention by bacterial PC-PLCs will lead to formation of choline phosphate and (optionally substituted) indoxyl (3-hydroxyindole). The (optionally substituted) indoxyl will dimerize quickly thereafter and then become oxidized by atmospheric oxygen or another oxidant forming a deeply colored indigo dye which is a well-known chromophor suitable for sensitive colorimetric detection by conventional method and apparatus means.

On plating media, indigo dyes will form characteristic and strongly colored precipitates which are substantially insoluble in aqueous media. As a consequence, the color formed will stay with the colony and does not diffuse throughout the plate. Also, the color formed will be clearly distinguishable from even a yellow-colored background of the medium. Thus, the novel compounds and substrates for PC-PLCs are very well suited for histochemical use. As will be shown below, media using substrates and compounds of formula (I) will generally improve and facilitate detection, and may even help to identify PC-PLC producing colonies of bacteria and other microorganisms.

According to a second embodiment, the invention provides substrates for detecting a phosphatidylcholine-specific phospholipase-C-enzyme as an indication of microbial or bacterial activity. The substrate comprises at least one chromogenic 3-indoxyl choline phosphate compound of formula (I), preferably in a suitable medium, such as typically aqueous agar-agar or similar gel-forming substances.

The term "substrate" as used herein and particularly in connection with formula (I) compounds is intended to indicate that at least one formula (I) compound is used for detecting PC-PLC in suitable media, such as aqueous agar-agar or conventional buffer solutions.

According to a third embodiment, the invention provides a method of detecting a phosphatidylcholine-specific phospholipase-C enzyme comprising the steps of contacting a sample suspected of containing the phosphatidylcholine-specific phospholipase-C enzyme with a substrate according to the invention containing at least one formula (I) compound wherein—as mentioned above—such compound(s) is/are susceptible to cleavage by the PC-PLC enzyme yielding a dye; and monitoring for color formation as a consequence of the PC-PLC enzyme suspected in the sample as a consequence of microbial activity.

According to a fourth embodiment, the invention provides a method of detecting microbial activity in a sample by combining the sample with substrate of formula (I) compound according to the invention and inspecting the resulting mixture by spectroscopic means, notably colorimetric means.

According to a fifth embodiment, the invention provides a kit which includes at least one compound of formula (I) for use in detecting PC-PLC as an indication of microbial activity.

According to another embodiment, the invention provides a continuous assay method for detecting PC-PLC by spectrophotometric means.

According to a further embodiment, the invention provides methods for detecting the presence of pathogenic strains—in a sample suspected to contain such strains—of one or more of the following species: *Clostridium perfringens, Bacillus cereus, Bacillus anthracis, Bacillus thuringiensis, Pseudomonas aeruginosa, Listeria monocytogenes, Heliobacter pylori,* and *Legionella pneumophila.*

According to a further embodiment, the invention provides for a method of identifying a bacterial microorganism capable of producing a phosphatidylcholine-specific phospholipase-C (PC-PLC) enzyme comprising the steps of:

(A) providing a test sample suspected of containing the microorganism of interest;

(B) preferably submitting the test sample to an enrichment broth step;

(C) transferring a portion, at least, of the test sample or the product obtained in step (B) to a medium suitable for culturing the microorganism; the medium containing at least one formula (I) compound capable of producing a color when exposed to the microorganism;

(D) cultivating the medium with the transferred portion for developping at least one colony exhibiting said color; and (E) recovering a portion, at least, of the colored colony for final identification.

According to yet another embodiment, the invention provides a method of producing a compound of formula (I) by the steps of:

reacting the corresponding (optionally N-protected) indoxyl-3-dichlorophosphate (formula (II) below) with a choline salt, such as a choline halide, typically the chloride or iodide, to form an intermediate compound (formula (III) below), e.g. by stirring the reactants in an organic base, such as quinoline, triethylamine, N-methylmorpholine or pyridine, as a reaction medium at an ambient temperature, typically 15–30° C., during a period of about one or more hours, e.g. 1–8 hours:

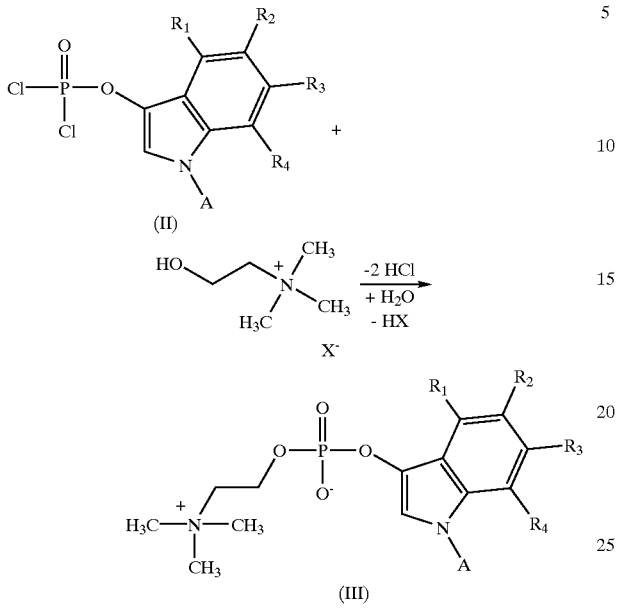

in which A represents hydrogen or a conventional protecting group for nitrogen, such as $C_{1-4}$ alkyl (preferably methyl), acyl (preferably acetyl or benzoyl) or an N-protecting group of the type known from peptide chemistry as Boc, CBZ, Fmoc etc.; and wherein X is an anion derived from an inorganic or organic acid, e.g. hydrochloric acid or citric acid; and $R^1$–$R^4$ have the meaning defined in connection with formula (I) above.

To complete synthesis of formula (I) compounds, the optional N-protecting group on the intermediate of formula (III) is removed—e.g. by acidic or mild basic cleavage or hydrogenolysis, depending upon the nature of the group or by other conventional methods known from peptide chemistry—in the subsequent second process step; if required or desired, group R is introduced by a conventional reaction.

From the above it will be apparent that compounds of formula (I) including preferred species thereof as defined below can be produced economically and in commercial quantities as required for use as substrates for application in standard screening procedures or plating media.

According to yet a further aspect, the invention provides for a method of preparing a substrate capable of detecting microbial phosphatidylcholine-specific phospholipase-C enzyme wherein the method comprises the step of producing the substrate by incorporating therein a 3-indoxyl choline phosphate compound of formula (I).

Preferred Embodiments of the Invention

In a group of formula (I) compounds—preferred because of high chromogenicity—R is selected from hydrogen or methyl, $R^1$ is selected from the group consisting of hydrogen and halogen (chlorine and fluorine being frequently preferred), $R^2$ is selected from the group consisting of hydrogen, cyano, nitro and halogen (bromine and iodine being frequently preferred), and $R^3$ and $R^4$ are independently selected from the group consisting of hydrogen and halogen (chlorine and fluorine being frequently preferred).

A particularly preferred specific novel compound is 5-bromo-4-chloro-3-indoxyl choline phosphate, i.e. a compound of formula (IV) below:

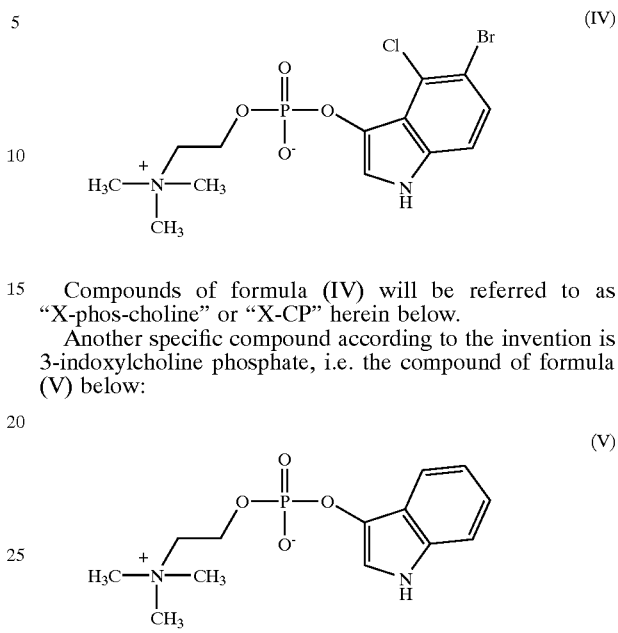

Compounds of formula (IV) will be referred to as "X-phos-choline" or "X-CP" herein below.

Another specific compound according to the invention is 3-indoxylcholine phosphate, i.e. the compound of formula (V) below:

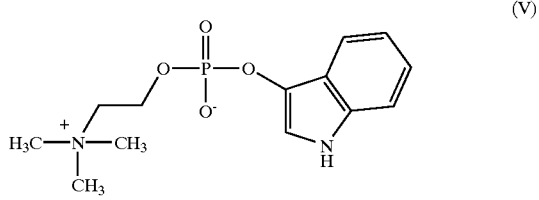

Compounds of formula (V) will be referred to as "Y-phos-choline" or "Y-CP" herein below.

Both compounds are white crystalline powders freely soluble in water. Tests made with X-phos-choline (X-CP) and Y-phos-choline (Y-CP) indicated that compounds (I) and substrates containing them are stable during extended periods of time at temperatures below about 5° C. when protected from light. Thus, similar properties can be reasonably expected for other formula (I) compounds.

Based upon the tests made with X-phos-choline and Y-phos-choline, formula (I) compounds proved to be stable in conventional buffer solutions (e.g. citrate/hydrochloric acid; Hepes/NaOH; Tris/HCl; boric acid/potassium chloride-sodium hydroxide) for at least ten days at a pH ranging from about 4 to about 10 at ambient temperature as well as in conventional plating media, e.g. Tryptic Soy Agar. Thus, problems with background signals caused by slow non-enzymic hydrolysis in the buffer media (as observed with the prior art substrate 4-nitrophenyl choline phosphate) are avoided. Again, similar properties can reasonably be expected for other formula (I) compounds.

The 5,5'-dibromo-4,4'-dichloroindigo generated from cleavage of X-CP by PC-PLCs, dimerization, and subsequent oxidation is a dye known per se and has a broad absorption ranging from ≈500 nm to ≈700 nm with a maximum at 652 nm. This dye has an intense brilliant blue color with an absorption coefficient at about 6000 L mol$^{-1}$ cm$^{-1}$.

A further preferred group of compounds of formula (I) particularly suitable for the purposes of the present invention are:
4-chloro-3-indoxyl choline phosphate,
5-bromo-3-indoxyl choline phosphate,
5-bromo-6-chloro-3-indoxyl choline phosphate (termed "Magenta-CP" herein),
6-chloro-3-indoxyl choline phosphate (termed "Salmon-CP") herein and
6-fluoro-3-indoxyl choline phosphate.

Magenta-CP and Salmon-CP are special within this group since their cleavage by PC-PLCs, dimerization, and subsequent oxidation generates dies of a characteristic red color.

According to an important aspect of the invention, formula (I) compounds and substrates containing them are used for a continuous spectrophotometric assay of PC-PLC, e.g. from *Clostridium perfringens* or other microbial species. As indicated above, addition of sorbitol or glycerol in high concentrations (up to about 60%) to conventionally used 4-nitrophenyl choline phosphate accelerates enzymatic cleavage of 4-nitrophenyl choline phosphate by *Clostridium perfringens* PC-PLC resulting in an assay for detection of PC-PLC with reasonable but very low cleavage rates.

Figure 7:
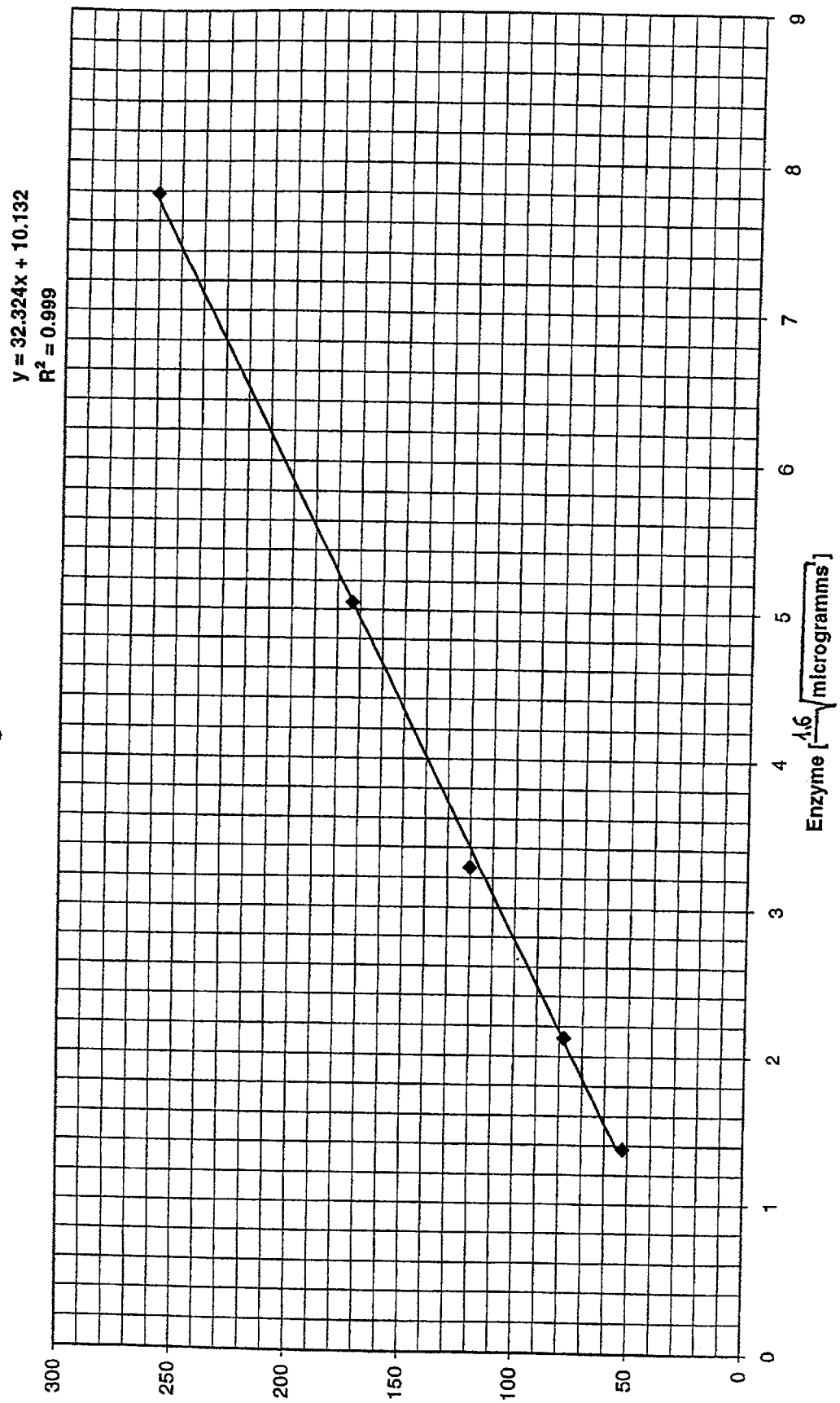

Addition of deoxycholic acid, glycerol or notably sorbitol to formula (I) compounds and substrates containing them, on the other hand, did not improve enzymatic reaction impact upon formula (I) compounds but rather inhibited the reaction.

Moreover, raising the temperature to about 60° C. did not accelerate the enzymatic hydrolysis markedly though the temperature optimum for the cleavage of the prior art substrate 4-Nitrophenyl choline phosphate by PC-PLC of *Clostridium perfringens* is reported at 65° C. (cf. J.-H. Weitkamp; Zentralblatt für Bakteriologie 280 (1993), 15).

Unexpectedly it has been found that the cleavage rate is considerably enhanced when use is made of at least one additive selected from the group consisting of serum albumin, surfactants and metal ions, wherein the metal ion is preferably selected from a divalent ion of cobalt, manganese, nickel, zinc, calcium or magnesium.

According to a further preferred embodiment, a substrate according to the invention additionally comprises at least one metal ion and at least one member selected from the group consisting of surfactants and serum albumin, wherein the metal ion preferably is a divalent ion of cobalt, manganese, nickel, zinc, calcium or magnesium.

The additive preferably selected, or the combination of additives, depend on the microorganism to be detected. It is to be noted that the preferred additive or additive combination enhanced the enzymatic cleavage by a factor of at least 100 as compared to prior art providing an enhancement factor of 2 or 3 (cf. J.-H. Weitkamp et al.; Zentralblatt für Bakteriologie 280 (1993), 11 and W. B. Baine; Journal of General Microbiology 134 (1988), 489).

This is surprising and was not to be expected since a certain amount of phospholipid chain hydrophobic binding seemed to be important for this water-soluble surface-active enzyme for the "natural substrates" of PC-PLC, e.g. the phosphatidylcholines. Also, fatty acid carbonyls (preferably unhindered) have been described as being more critical in productive binding and subsequent hydrolysis (cf. El-Sayed et al; Biochimica et Biophysica Acta 837 (1985), p. 326). Furthermore, El-Sayed et al. have indicated that fatty acid chains must be sufficiently long to produce a hydrophobic binding site on the lipid molecule (cf. El-Sayed et al.; Biochimica et Biophysica Acta 837 (1985), p. 333). However, the compounds according to the invention are very polar and lack any hydrophobic sites, e.g. longer alkyl chains, as well as fatty acid carbonyls.

Thus, using a preferred and proper additive, or combination of additives, substrates according to the invention can be utilized for a much more sensitive assay of PC-PLC from a particular microorganism. Typically, a preferred suitable additive or combination of additives will be evaluated individually for each microorganism to be detected, or for each PC-PLC to be assayed. This can be done by those experienced in the art by means of a few and simple experiments, e.g. as exemplified below.

Typically, a compound according to the invention is used in combination with at least one enhancer selected from bovine serum albumin (BSA), certain divalent metal ions, e.g. of cobalt, manganese, nickel, zinc, magnesium or calcium, and a surfactant, preferably a nonionic surfactant, such as polysorbates, and even more preferred Tween® 80 (polyoxyethylene sorbitan monooleate), depending on the PC-PLC of the microorganism to be assayed.

While no limitation by theory is intended, the special effect of BSA is believed to result from the hydrophobic character of the protein which property is known to enhance reactions of enzymes that normally act on hydrophobic substrates, e.g. PC-PLC enzymes cleaving phosphatidylcholine.

In a particularly preferred embodiment, a substrate according to the invention comprises at least one compound of formula (I), preferably X-CP, and a combination of BSA and a divalent salt of cobalt, preferably cobalt(II)sulfate. This combination has been found to provide an extreme cleavage enhancement of X-CP by *Clostridium perfringens* PC-PLC. Thus, using this combination, together with X-CP, a most sensitive determination of PC-PLC from *Clostridium perfringens* has been made available.

If compared with 4-nitrophenyl choline phosphate in prior art substrates, compounds and substrates according to the invention provide further advantages because assay of PC-PLC can be carried out in common buffer solutions, preferably by adding just small amounts of additives: When using 4-nitrophenyl choline phosphate, a reasonable rate of enzymatic hydrolysis required use of viscous solutions of such prior art substrates in sorbitol.

A further important aspect of the invention concerns use of compounds of formula (I), e.g. the particularly preferred 5-bromo-4-chloro-3-indoxyl choline phosphate (X-phoscholine; X-CP) or 3-indoxyl choline phosphate (Y-phoscholine; Y-CP) for the detection of PC-PLC in microorganisms, preferably by spectroscopic means and notably by calorimetric means.

As clearly indicated by the data from the subsequent examples, chromogenic substrates X-CP and Y-CP can be used on conventional plating media to detect PC-PLC by formation of a turquoise-to-blue colony color. The color stays within the colony because insolubility prevents migration of the dye to the medium.

BRIEF DESCRIPTION OF THE DRAWINGS

The invention will now be explained without limitation in more detail by way of examples and with reference to the enclosed drawings in which:

FIG. 1 is a graph showing dependence of the absorbance (on the ordinate) upon time (on the abscissa) at various temperatures obtained with the inventive substrate comprising X-phos-choline (X-CP) upon cleavage with PC-PLC from *Clostridium perfringens* (cf. Example 4);

FIG. 2 is a graph similar to that of FIG. 1 except that the curves are shown at various concentrations of X-CP at a temperature of 58–59° C. (cf. Example 5);

FIG. 3 is a Lineweaver-Burk plot of 1/cleavage rate (ordinate; in min/nMol) versus 1/X-CP concentration (abscissa; in 1/mMol) (cf. Example 5);

FIG. 4 is a graph showing dependence of the absorbance (ordinate) upon time (abscissa) at 0.01, 0.02, 0.05, 0.1 and 0.2 units (U) of *Clostridium perfringens* PC-PLC obtained with a substrate comprising X-CP at 58–59° C. (cf. Example 6);

FIG. 5 is a graph similar to FIG. 4 for 0.5, 1, 2, 4 and 8 units of enzyme; and FIG. 6 is a graph showing the rate of cleavage of X-CP (ordinate; in nMol/min) versus amount of enzyme (abscissa;

in μg) in the range of 0.01 to 0.5 units (U), i.e. 33 ng to 1667 ng, of *Clostridium perfringens* PC-PLC (cf. Example 6); and FIG. 7 shows a linear relationship between the rates of cleavage of X-CP (ordinate) and the expression $^{1,6}\sqrt{\text{amount}}$ of enzyme (abscissa) in the range of 0.5 to 8 units (U), i.e. 1.66 to 27 μg of enzyme (Example 6).

EXAMPLES

Preparation of Compounds of Formula (I)

1-Acetyl-5-bromo-4-chloro-3-indoxyl-dichlorophosphate (1-acetyl-5-bromo-4-chloro-3-indoxyl-phosphorodichloridate) was prepared in a manner known per se, cf. J. P. Horwitz, J. V. Freisler; Journal of Medicinal Chemistry 13 (1970), 1024. 1-Acetyl-3-indoxyl-dichlorophosphate was prepared in an analog manner. Choline iodide was synthesized according to the procedure of B. Chesebro and H. Metzger (cf. Biochemistry 11 (1972), 766).

Example 1

Preparation of X-phos-choline (IV)

Step 1: Preparation of 1-Acetyl-5-bromo-4-chloro-3-indoxyl choline phosphate

1-Acetyl-5-bromo-4-chloro-3-indoxyl-dichlorophosphate (4.06 g, 10 mMol) was suspended under nitrogen in dry acetonitrile (12 ml) and choline iodide (2.31 g; 10 mMol) was added. The mixture was stirred at ambient temperature while quinoline (1.46 ml; 10 mMol) was added dropwise within a period of five minutes. Choline iodide dissolved slowly. A slightly turbid solution was obtained after one hour and stirred at the same temperature for a period of another 2 hours.

After removing some solid matter by filtration the clear brownish-yellow filtrate was added dropwise to a cooled (0–5° C.) solution of pyridine (5.6 ml; 70 mMol) in water (20 ml).

The solution was evaporated under reduced pressure to yield a yellow-brown oil which was dissolved in water (60 ml). Mixed-bed exchange resin MB-150 (Sigma # A-5710; 60 g) was added and agitation was continued for a period of 20 minutes. The pH was adjusted to ≈5 by addition of a 25% ammonium hydroxide solution in water (1.5 ml) and the resin was removed by filtration through a glass filter funnel and washed with water.

Ethanol (10 ml) was added to the filtrate to prevent foaming, and the solution was carefully concentrated by rotary evaporation under reduced pressure to a volume of 40 ml. Upon cooling to ambient temperature colorless crystals of the product were obtained. The suspension was stored at 5° C. overnight. The product was collected by filtration and washed twice with ice water (2×2 ml), once with acetone (5 ml), and finally dried in vacuum to yield 1.28 g of a white crystalline powder. Another 0.20 g and 0.24 g of material were obtained from the mother liquor and the acetone washing, respectively. Overall yield was 1.72 g (37%), m.p. 241–243° C. (dec.).

Analysis calcd. for $C_{15}H_{19}BrClN_2O_5P$ (MW=453.65): C 39.71, H 4.22, N 6.18, Br 17.61, Cl 7.82, P 6.83; Found (calcd. on dry matter; water content 3.95%): C 39.70, H 4.25, N 6.12, Br 17.49, Cl 7.83, P 6.72; $^1$H-NMR (400 MHz; DMSO-$d_6$), δ (ppm): 8.22 (d; 1H), 7.65 (broadened s, 1H), 7.62 (d; 1H), 4.18 (m, 2H), 3.55 (m, 2H), 3.11 (s, 9H), 2.56 (s, 3H). $^{13}$C-NMR (400 MHz; DMSO-$d_6$), δ (ppm): 169.0, 135.8 (d, $J_{P,C}$=6.4 Hz), 132.6, 129.3, 123.8, 123.2 (d, $J_{P,C}$=6.6 Hz), 116.9, 116.0, 113.6 (small d, $J_{P,C}$=2.4 Hz), 65.4 (m), 59.0 (d, $J_{P,C}$=5.6 Hz), 53.1 (t, $J_{N,C}$=3.5 Hz), and 23.7.

Step 2: Preparation of 5-Bromo-4-chloro-3-indoxyl choline phosphate (IV)

1-Acetyl-5-bromo-4-chloro-3-indoxyl choline phosphate (0.51 g; 1.1 mMol) was dissolved in a 2 N solution of ammonia in methanol (10 ml) under nitrogen. The educt quickly dissolved leaving a greenish-yellow solution. After a period of 2 hours the solvent was removed in vacuo.

The greenish-beige foam thus obtained was dissolved in warm (≈50° C.) ethanol (2 ml), and acetone (4 ml) was added. The solution was seeded and a few minutes later a white crystalline precipitate was formed. The suspension was stirred for 30 minutes at ambient temperature whereupon additional acetone (1 ml) was added. The suspension was filtered after 60 minutes through a glass filter funnel and the crystals washed with acetone (2×2 ml). The product was dried in vacuo yielding 0.36 g (80%) of an almost colorless crystalline powder. m.p. 247–248° C. (dec.).

Analysis calcd. for $C_{13}H_{17}BrClN_2O_4P$ (MW=411.62): C 37.93, H 4.16, N 6.80, Br 19.41, Cl 8.61, P 7.52; Found (calcd. on dry matter; water content 5.3%): C 37.90, H 4.20, N 6.82, Br 19.23, Cl 8.48, P 7.40; $^1$H-NMR (400 MHz; $D_2O$), δ (ppm): 7.22 (small d; 1H), 7.19 (d, 1H), 7.06 (d; 1H), 4.28 (broad s, 2H), 3.43 (t, 2H, $J_{P,H}$=4.4 Hz), 2.95 (s, 9H); $^{13}$C-NMR (400 MHz; $D_2O$), δ (ppm): 133.5, 129.9 (d, $J_{P,C}$=7.5 Hz), 126.9, 123.1, 118.4 (d, $J_{P,C}$=4.9 Hz), 115.7 (broadened s), 113.4, 112.8, 66.5 (m), 60.5 (d, $J_{P,C}$=5.2 Hz), 54.2 (broadened s). UV (0.1 N HEPES/NaOH pH 7.0): $\lambda_{max}$=290 nm, ε=4910 L $Mol^{-1}$ $cm^{-1}$.

Example 2

Preparation of 3-Indoxyl choline phosphate (V)

Step 1: Preparation of 1-Acetyl-3-indoxyl choline phosphate

1-Acetyl-3-indoxyl-dichlorophosphate (8.76 g, 30 mMol) was suspended under nitrogen in dry acetonitrile (36 ml) and choline iodide (6.93 g; 30 mMol) was added. The mixture was stirred at ambient temperature while quinoline (4.38 ml; 30 mMol) was added dropwise during 15 minutes. The choline iodide dissolved slowly, and a slightly turbid solution was obtained after 30 minutes. The solution was stirred at the same temperature for another hour. The brownish-yellow solution was then added dropwise to a cooled (0–5° C.) solution of pyridine (16.8 ml; 210 mMol) in water (60 ml).

The solution was evaporated at 55–60° C. under reduced pressure to yield a yellow-brown oil which was dissolved in water (60 ml). A small amount of solids was removed by filtration. Water (105 ml) was added to the filtrate, and a mixed-bed exchange resin MB-150 (Sigma # A-5710; 90 g) was added. Agitation was continued for 10 minutes. The resin was removed by filtration and washed with water.

The yellow-orange filtrate obtained was concentrated carefully by rotary evaporation at 55–60° C. under reduced pressure to a volume of 5–10 ml. Colorless crystals of the product appeared spontaneously upon cooling to ambient temperature. The suspension was stirred for half an hour at the same temperature and subsequently stored at 5° C. overnight. The product was collected by filtration and washed once with ice-water (4 ml), once with acetone (6 ml), and finally dried under vacuum to yield 4.38 g (43%) of a white crystalline powder. m.p. 259–260° C. (dec.).

Analysis calcd. for $C_{15}H_{21}N_2O_5P$ (MW=340.31): C 52.94, H 6.22, N 8.23, P 9.10; Found (calcd. on dry matter; water content 11.6%): C 52.81, H 6.35, N 8.18, P 8.99; $^1$H-NMR (400 MHz; DMSO-$d_6$), δ (ppm): 8.10 (broad d; 1H), 7.57 (m, 1H), 7.33 (m; 3H) 4.36 (m, 2H), 3.58 (t, 2H, $J_{P,H}$=4.5 Hz), 3.08 (s, 9H), 2.51 (s, 3H). $^{13}$C-NMR (400 MHz; DMSO-$d_6$), δ (ppm): 171.7, 135.7 (d, $J_{P,C}$=7.7 Hz), 132.5, 126.0, 124.2 (d, $J_{P,C}$=5.2 Hz), 123.8, 117.4, 115.8, 112.2 (very small d), 65.6 (m), 59.9 (d, $J_{P,C}$=5.2 Hz), 53.6 (t, $J_{N,C}$=3.5 Hz), 22.9.

Step 2: Preparation of 3-Indoxyl choline phosphate (V)

A 2 N solution of ammonia in methanol (28 ml) was added under nitrogen at a temperature of 10–20° C. to 1-acetyl-3-indoxyl choline phosphate (2.72 g; 8 mMol). The educt dissolved quickly yielding a slightly blue solution. Acetone (80 ml) was added after a period of 3 hours. The solution was seeded whereupon a white crystalline precipitate was formed rapidly. The suspension was stirred half an hour at ambient temperature and then for two hours in an ice bath. The product was collected by filtration through a glass filter funnel and the crystals washed with acetone (2×20 ml). The product was dried in vacuo yielding 1.58 g (66%) of a white crystalline powder. m.p. 261–262° C. (dec.).

Analysis calcd. for $C_{13}H_{19}N_2O_4P$ (MW=298.28): C 52.35, H 6.42, N 9.39, P 10.38; Found (calcd. on dry matter; water content 0.6%): C 52.42, H 6.55, N 9.45, P 10.26; $^1$H-NMR (400 MHz; $D_2O$), δ (ppm): 7.52 (d; 1H), 7.30 (d, 1H), 7.08 (td; 1H), 7.06 (d, 1H), 7.00 (td, 1H), 4.11 (m, 2H), 3.27 (t, 2H, $J_{P,H}$=4.25 Hz), 2.75 (s, 9H); $^{13}$C-NMR (400 MHz; $D_2O$), δ (ppm): 132.7, 129.7 (d, $J_{P,C}$=7.8 Hz), 122.0, 119.3 (d, $J_{P,C}$=4.4 Hz), 119.0, 116.6, 112.5, 111.6, 65.3 (m), 59.6 (d, $J_{P,C}$=5.0 Hz), 53.1. UV (0.1 N HEPES/NaOH pH 7.0): $\lambda_{max}$=280 nm, ε=5020 L Mol$^{-1}$ cm$^{-1}$.

Example 3

Evaluation of the Proper and Preferred Additive or Combination of Cleavage Rate Enhancers for *Clostridium perfringens* PC-PLC Simple test tube experiments were conducted to select a preferred additive or additive combination for quick color formation from X-phos-choline (X-CP) by enzymatic hydrolysis with PC-PLC of *Clostridium perfringens.*

Preliminary tests at ≈40° C. showed that a slight enhancement of the cleavage rate of the enzyme was obtained when using octyl-β-D-thiogalactopyranoside (Biosynth O-2700) at 0.1%; octyl-β-D-thioglucopyranoside (Biosynth O-2710) at 0.1%; N-nonanoyl-N-methyl-glucamin (Fluka 74315) in the range 0.1% to 1%; and the sodium salt of glycocholic acid (Sigma G-7132) at 0.1%, to X-CP (the values given in % indicate the additive concentration in weight per volume). For all these detergents and surfactants, respectively, no additional enhancement was observed when combined with BSA.

Further experiments were conducted at 60° C., which is near the temperature optimum of the enzyme, cf. example 4. The basic parameters were as follows:

≈1,7 mg of X-CP were dissolved in 1 ml of 0.1 N HEPES/NaOH-buffer of pH 7.0 yielding a ≈4 nMol solution of the substrate.

The following chemicals were added to the buffer, either alone or in combination, for testing acceleration of enzymatic cleavage:

| | |
|---|---|
| Bovine Serum Albumin (Fluka 05470) at 0.1% | (BSA) |
| Magnesium sulfate heptahydrate (Fluka 63140) at 0.01% | ($Mg^{2+}$) |
| Calcium chloride dihydrate (Fluka 21098) at 0.01% | ($Ca^{2+}$) |
| Manganese(II)sulfate monohydrate (Fluka 63554) at 0.01% | ($Mn^{2+}$) |
| Cobalt(II)sulfate heptahydrate (Fluka 00622) at 0.01% | ($Co^{2+}$) |
| Nickel(II)sulfate hexahydrate (Fluka 72280) at 0.01% | ($Ni^{2+}$) |
| Zinc sulfate heptahydrate (Fluka 96500) at 0.01% | ($Zn^{2+}$) |

One unit (U) of phospholipase C from *Clostridium perfringens* (Sigma P-4030, cf. examples 4–6 below) was added to each solution. The tubes were checked visually after defined periods of time. Table 1 shows the color of the solution using various combinations of the above reagents after 1 hour at 60° C.

TABLE 1

| Combination | No Additive | $Mg^{2+}$ | $Ca^{2+}$ | $Mn^{2+}$ | $Co^{2+}$ | $Ni^{2+}$ | $Zn^{2+}$ |
|---|---|---|---|---|---|---|---|
| No Additive | Bluish | Bluish | Colorless | Pale blue | Light blue | Pale blue | Colorless |
| BSA | Bluish | Bluish | Colorless | Light blue | Deep dark blue | Colorless | Colorless* |

*precipitation of zinc hydroxide!

Table 1 clearly shows the drastic effect of additives upon the rate of cleavage. Thus, addition of BSA and $Co^{2+}$ to a substrate comprising X-CP strongly accelerate the cleavage rate for *Clostridium perfringens* PC-PLC. The enhancement with the combination of BSA and cobalt ions is of such outstanding order as to make X-phos-choline (X-CP) a very useful compound and substrate, respectively, for detecting PC-PLC of *Clostridium perfringens.*

Remarkable variations in the rate enhancement are observed, however, requiring proper selection of additive or combination of additives to obtain an optimal rate enhancement. Compared with the BSA/$Co^{2+}$ system, the addition of manganese or nickel ions accelerates the cleavage rate only moderately whereas calcium and zinc ions have an inhibiting effect. In combination with BSA, manganese ions cause but a weak enhancement whereas nickel ions cause inhibition. As is apparent, optimum selection of additive(s) for a large cleavage rate enhancement may depend upon the specific microorganism and, thus, may be amenable to optimization by simple tests as exemplified above.

Examples 4–6

Colorimetric Assay of PC-PLC from *Clostridium perfringens* using X-phoscholine A spectrophotometer known as Pye Unicam SP 6-450 UV/VIS was used in these examples. The spectrometer was set for 652 nm.

General procedure for the tests in Example 5 and 6 was as follows:

All components were dissolved in 0.1 M HEPES/NaOH-buffer of pH 7.0. In a cuvette (3 ml volume) bovine serum albumin (BSA; Fluka 05470) and differing amounts of cobalt salts were dissolved in 2 ml of buffer solution. An aliquot from a stock solution of PC-PLC from *Clostridium perfringens* (Sigma P-4039: Type XIV, chromatographically purified, lyophilized powder in buffered salts; activity: 300 units (U) per mg protein (Lowry) using egg yolk phosphatidylcholine) were added. The stock solution of the enzyme was prepared by dissolving the powder in the above buffer to yield a final concentration of 1 Unit/10 μL solution. The mixture in each cuvette was incubated 30 minutes at 60° C.

In the meantime, X-phos-choline (X-CP) was dissolved in 1 ml of the buffer. This solution was transferred to the cuvette to start enzymatic hydrolysis of X-CP and substrate, respectively. Photometer readings were noted after defined periods of time for various temperatures as well as for differing concentrations of the compound, the substrate, and the enzyme, respectively.

Example 4
Effect of Temperature

In a first set of experiments, the influence of temperature on the enzymatic cleavage of X-CP by PC-PLC from *Clostridium perfringens* was tested. In this case the cuvettes were not incubated prior to the addition of X-CP and substrate, respectively, but the reaction was started by adding the enzyme:

BSA and cobalt(II)chloride hexahydrate (Fluka 60820) were added to a solution of X-CP in the above mentioned buffer to yield the following final concentrations. Again, values given in % indicate the concentrations in weight per volume at volumes of 3 ml):

X-CP at 20 mM (24.7 mg/3 ml), BSA at 0.3%,
cobalt(II)chloride hexahydrate at 0.025% (1.05 mMol).
The cuvettes were incubated at ambient temperature (22° C.) as well as at 41° C., 46° C., 51° C., 55° C. and 60° C., respectively.

Each measurement was started by adding 2 units (U) of PC-PLC (Sigma P-4039, as above) to the cuvette.

FIG. 1 shows change of absorbance A as a function of time for various temperatures.

Reaction rates $\Delta c/\Delta t$ (c=concentration) of the enzymatic cleavage were calculated from slopes $\Delta A/\Delta t$ of the linear portion of each curve using the Lambert-Beer equation: $\Delta A = \epsilon \cdot \Delta c \cdot d$ (d=1 cm; absorption coefficient $\epsilon = 6000$ L mol$^{-1}$ cm$^{-1}$ for the 5,5'-dibromo-4,4'-dichloro indigo dye).

Specific activities were calculated from the rates considering the amount of enzyme (2 units (U)=6.667 μg) used.

Table 2 lists reaction rates (related to a volume of 3 ml) and specific activities [1 nMol min$^{-1}$ (μg protein)$^{-1}$=1 μMol min$^{-1}$ (mg protein)$^{-1}$] of *Clostridium perfringens* PC-PLC for the temperatures investigated.

TABLE 2

| Temperature [° C.] | Rate [nMol/min] | Specific Activity [μMol min$^{-1}$ mg$^{-1}$] |
|---|---|---|
| 22 | 0.65 | 0.1 |
| 41 | 8.1 | 1.2 |
| 46 | 19.7 | 3.0 |
| 51 | 25.8 | 3.9 |
| 55 | 48.5 | 7.3 |
| 60 | 106.8 | 16.0 |

Table 2 shows the marked influence of temperature on enzyme activity. For every 10° C. of rise in temperature the enzymatic activity increased by a factor of 3–4. For example, cleavage at 60° C. is approximately 160 times faster than at ambient temperature.

Example 5
Dependence upon Concentration of X-CP

Influence of the X-CP concentration was tested in this second set of experiments conducted at 58–59° C. Fixed parameters were as follows: BSA at 0.1%, cobalt(II)sulfate heptahydrate (Fluka 00622) at 0.01% (0.356 mM), 1 unit (U) of enzyme, cf. Example 4.

Figure 2:
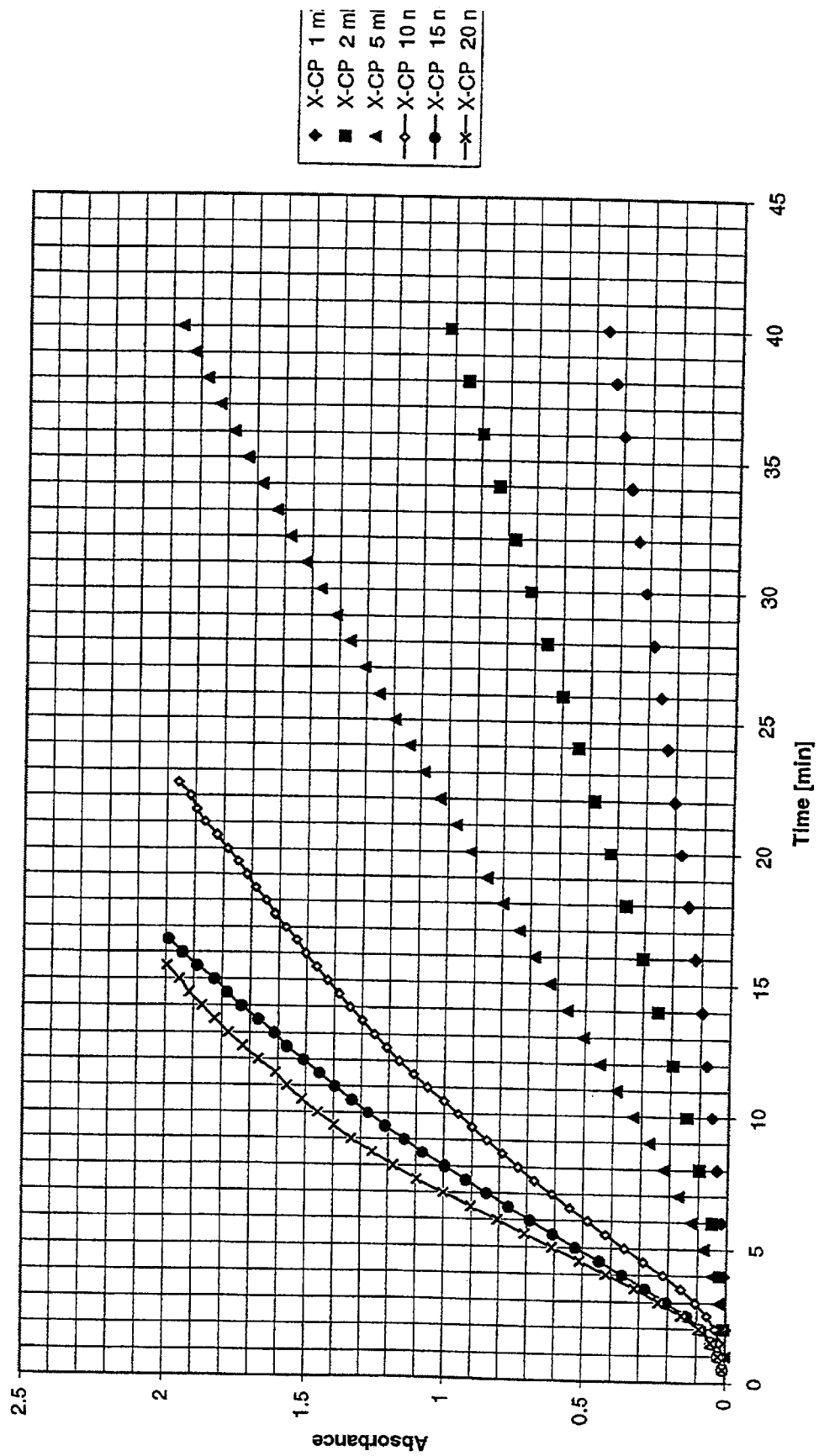

FIG. 2 shows the increase of the absorbance at 652 nm in dependence of time for the given concentrations of X-CP.

Table 3 shows rates of cleavage (again for 3 ml, the cuvette volume) and specific activities calculated as described in Example 4.

TABLE 3

| X-CP Concentration [mM] | Rate [nMol/min] | Specific Activity [μMol min$^{-1}$ mg$^{-1}$] |
|---|---|---|
| 1 | 7.2 | 2.15 |
| 2 | 14.7 | 4.4 |
| 5 | 30.0 | 9.0 |
| 10 | 64.1 | 19.2 |
| 15 | 83.3 | 25.0 |
| 20 | 100.8 | 30.25 |

PC-PLC activity was not entirely proportional to the X-CP concentration. For the higher concentrations of 15 mMol and 20 mMol, activity decreased thus indicating a Michaelis behavior of the PC-PLC activity. Similar behavior has been observed with the natural substrate phosphatidylcholine in a phospholipase C-alkaline phosphatase coupled assay (cf. E. L. Krug, C. Kent; Archives of Biochemistry and Biophysics 231 (1984), p. 406).

Figure 3:
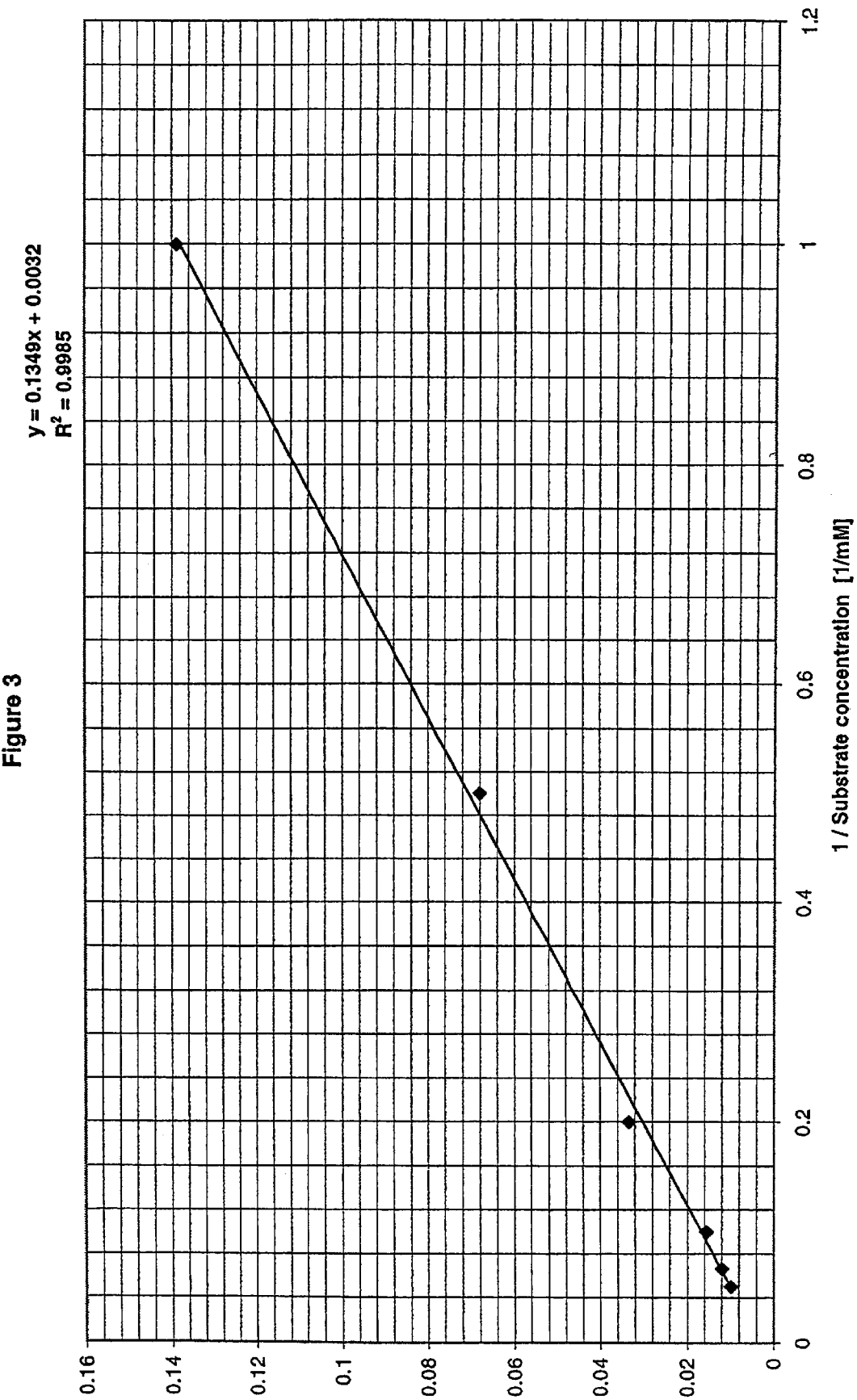

Thus, kinetic parameters could be determined from a Lineweaver-Burk plot of the inverse values of rate and concentration, i.e. 1/rate versus 1/substrate concentration, cf. FIG. 3. From a linear regression analysis of the data, values could be estimated for the rate of cleavage under saturating conditions $v_{max}$ and for the Michaelis-Menten constant $K_m$:

$V_{max}$=1/0.0032=312 nMol min$^{-1}$ (for 1 Unit of enzyme used=3.333 μg).

$V_{max}$=312 nMol min$^{-1}$ (3.333 μg enzyme)$^{-1}$=93.6 nMol min$^{-1}$ (μg enzyme)$^{-1}$≈94 μMol min$^{-1}$ (mg enzyme)$^{-1}$.

$K_m$=0.1349/0.0032≈42 mMol.

Such estimation of $K_m$ indicates a rather low affinity of the enzyme for X-CP. However, from the value of $V_{max}$ it is obvious that turnover of enzyme-bound X-CP is high enough to be useful in conducting enzyme assays, cf. Example 6.

Example 6

Dependence upon Enzyme Concentration

These tests were conducted to establish correlation between cleavage rates and amounts of enzyme applied. The parameters were as follows:

X-CP at 10 mM (12.35 mg/3 ml), BSA at 0.1%, cobalt (II)sulfate heptahydrate at 0.01%, cf. example 5.

All the cuvettes were incubated at 58–59° C.

Figure 4:
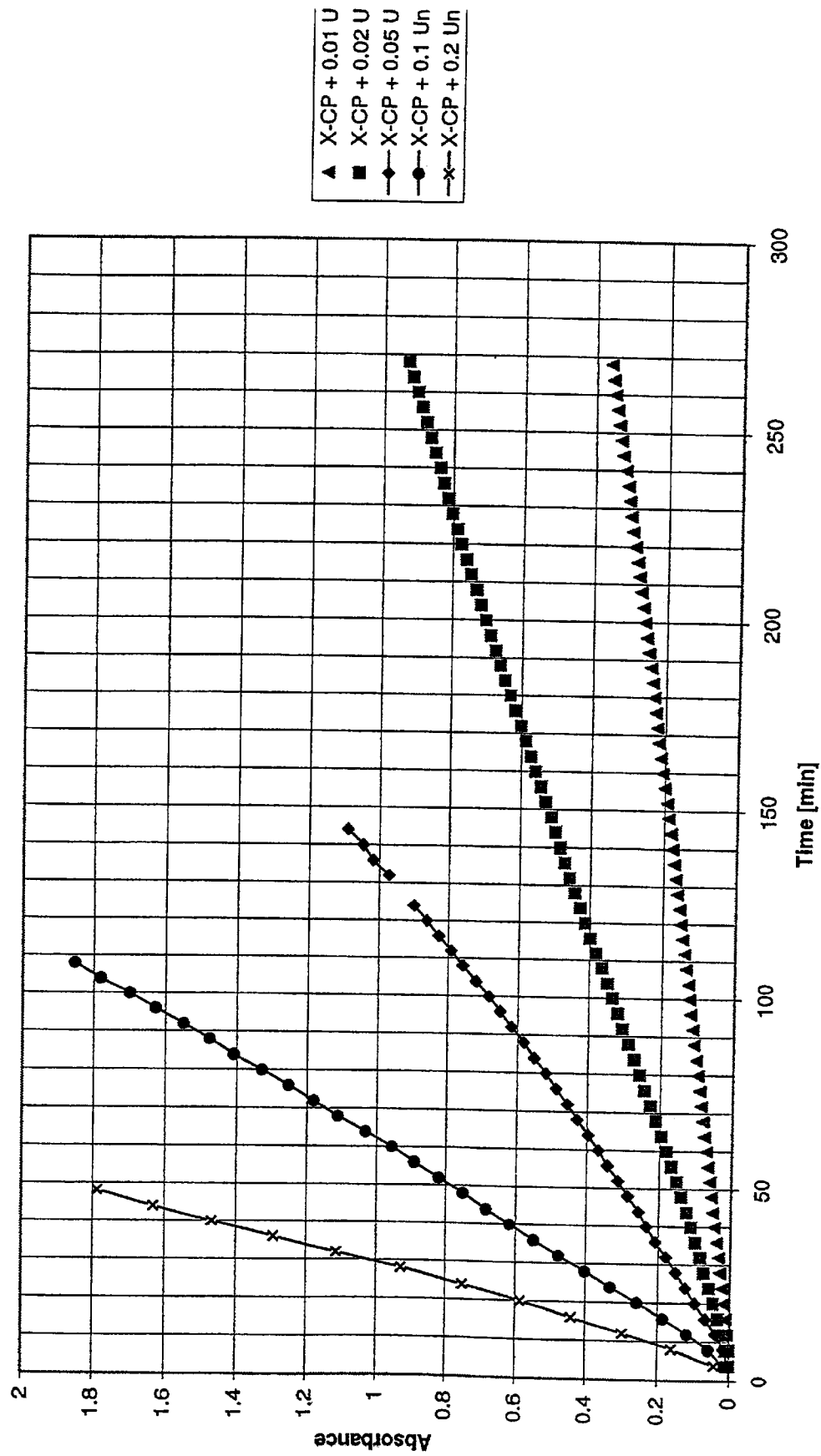
Figure 5:
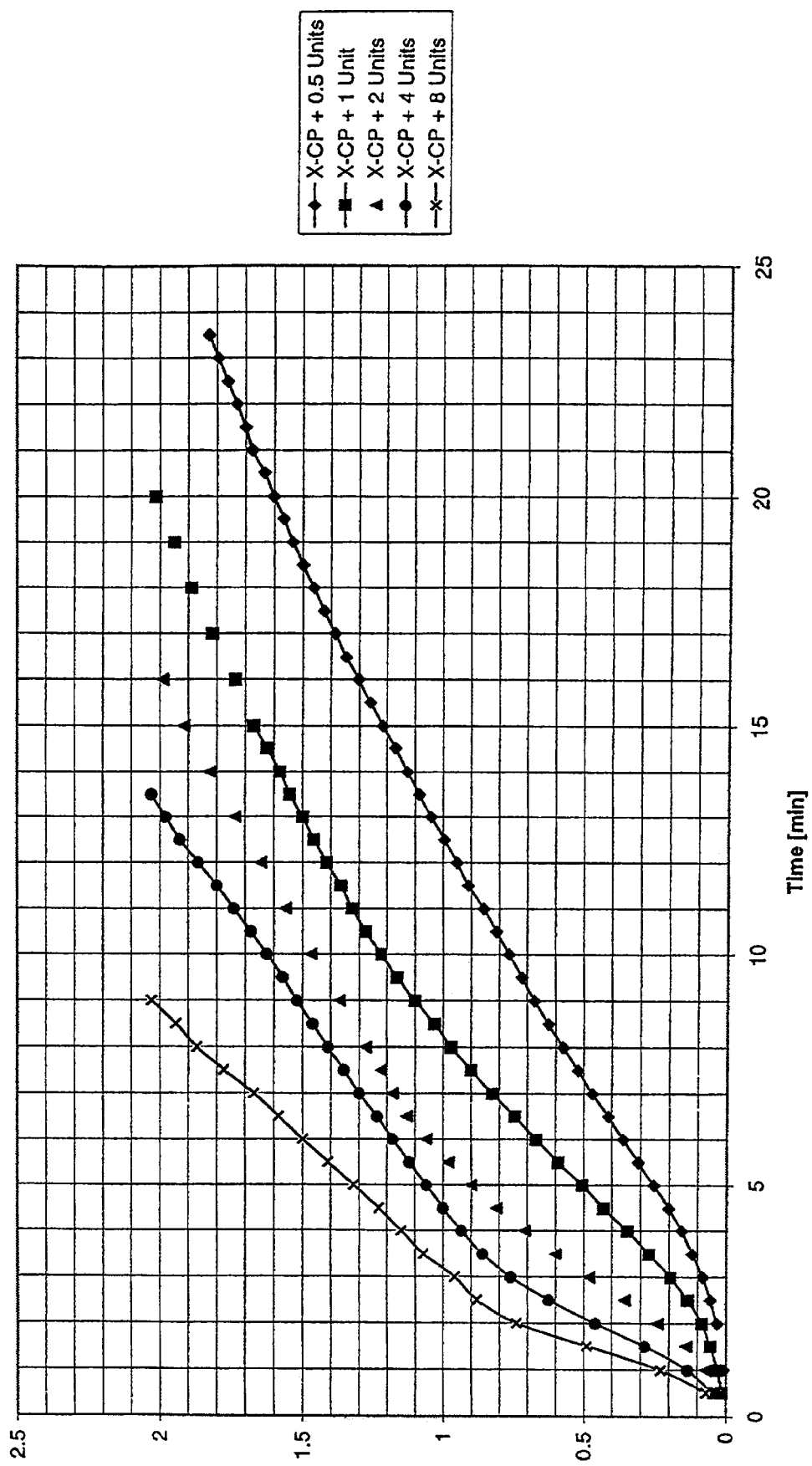

FIGS. 4 and 5 show time dependence of X-CP hydrolysis using 0.01 to 0.2 and 0.5 to 8 units (U) of PC-PLC from *Clostridium perfringens*, respectively.

Again, reaction rates were calculated from the slopes of the linear portion of the curves as described in Example 4. Table 4 shows rates of cleavage and specific activities for various amounts of enzyme used (1 unit (U)=3.33 μg enzyme, cf. general procedure above).

TABLE 4

| Enzyme | | $^{1,6}\sqrt{}$Enzyme | Rate | Specific Activity | CF |
|---|---|---|---|---|---|
| [Units] | [$\mu$g] | $^{1,6}\sqrt{[\mu g]}$ | [nMol/min] | [$\mu$Mol min$^{-1}$ mg$^{-1}$] | [$\mu$Mol min$^{-1}$ $^{1,6}\sqrt{[mg]}^{-1}$] |
| 0.01 | 0.0333 | 0.1193 | 0.74 | 22.2 | 6.2 |
| 0.02 | 0.0666 | 0.1841 | 1.9 | 28.2 | 10.2 |
| 0.05 | 0.1666 | 0.3263 | 4.7 | 28.4 | 14.5 |
| 0.1 | 0.3333 | 0.5033 | 9.4 | 28.2 | 18.7 |
| 0.2 | 0.6666 | 0.7761 | 22.0 | 33.0 | 28.3 |
| 0.5 | 1.6666 | 1.376 | 52.1 | 31.25 | 37.85 |
| 1 | 3.3333 | 2.122 | 78.6 | 24.0 | 37.05 |
| 2 | 6.6666 | 3.273 | 120.2 | 18.2 | 36.7 |
| 4 | 13.333 | 5.048 | 173.6 | 13.0 | 34.4 |
| 8 | 26.666 | 7.785 | 260.4 | 9.8 | 33.45 |

Table 4 indicates a nearly linear relation between reaction rates and amounts of enzyme present in the range of 0.02 to 0.5 units (U) while specific activity is reduced for 0.01 units (U) and declines substantially for the higher enzyme concentrations (≧1 U).

Figure 6:
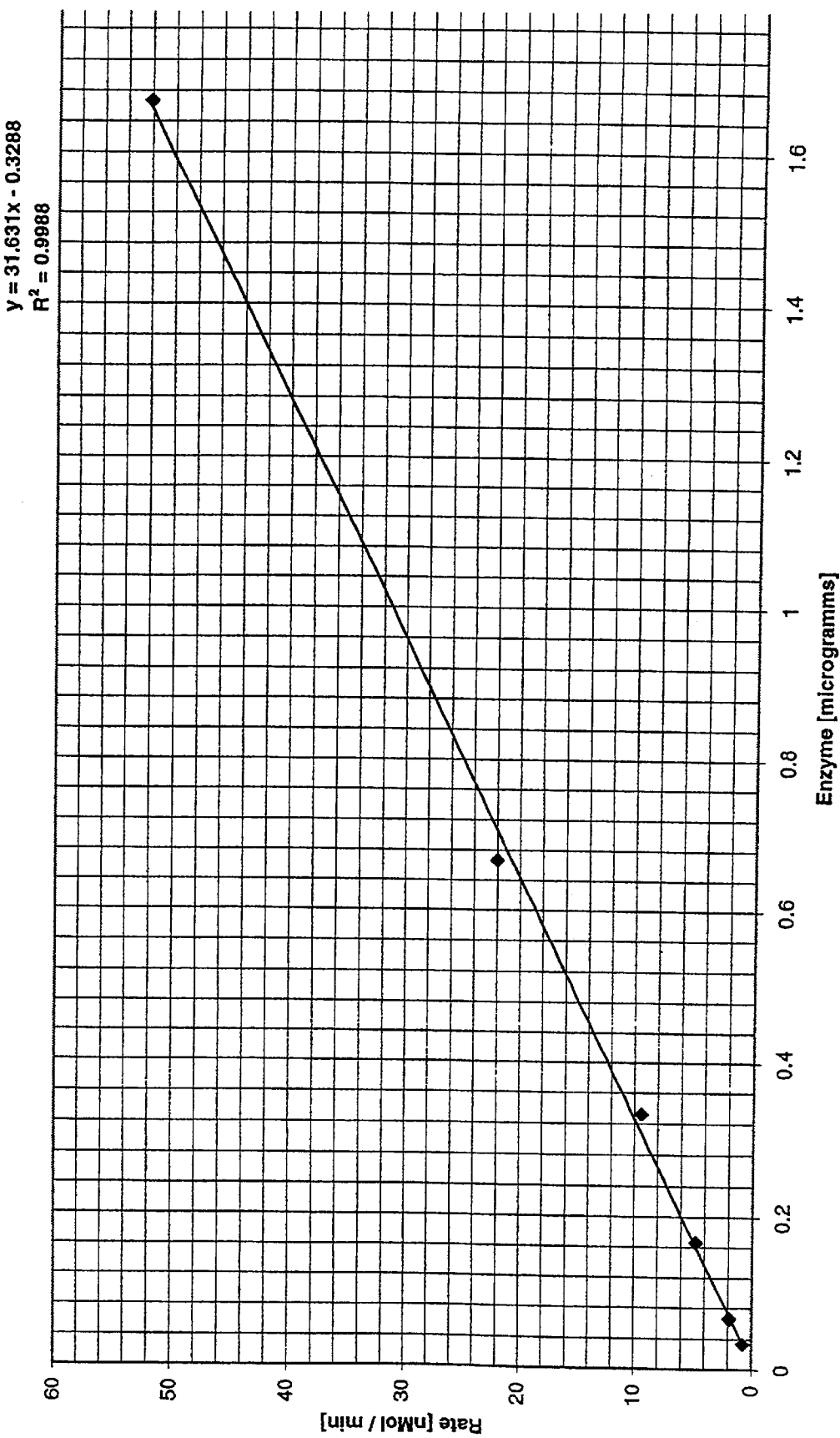

FIG. 6 is a plot of rates versus enzyme amount in the range of from 0.01 to 0.5 U (33 ng to 1667 ng). Proportionality between rate and amount of enzyme applied is evident.

No linearity was observed in the range of from 0.5 to 8 units (U) of enzyme. However, reaction rate is proportional to the expression $^{1,6}\sqrt{\text{amount}}$ of enzyme; the factor "CF" in Table 4 is nearly constant. FIG. 7 shows a linear relation between rates and $^{1,6}\sqrt{\text{amount}}$ of enzyme in the range 0.5 to 8 U (1.66 to 27 $\mu$g) of enzyme present. Thus, using a substrate comprising X-CP, the PC-PLC enzyme of *Clostridium perfringens* can be assayed quite accurately, at least in a range from 33 ng to 27 $\mu$g. This example shows that such an assay is of practical value even at simple, i.e. non-optimized conditions.

Example 7

(a) Preparation and Inoculation of Plating Media for Testing the Efficacy of X-CP and Y-CP Microbial Strains

*Bacillus cereus* (ATCC 13061), *Bacillus thuringiensis* (ATCC 33680), and *Pseudomonas aeruginosa* (ATCC 15442) were stored at 4° C. on Difco Brain Heart Infusion Agar (BHIA) slants. Cultures were transferred to a fresh BHIA slant monthly. A loopful of *B. cereus, B. thuringiensis,* and *P. aeruginosa* cells was aseptically transferred to Difco Brain Heart Infusion Broth (BHIB) and incubated at 35° C. for 24 hours. After incubation, these cells were used to streak the test plating media for the colorimetric detection of PC-PLCs.

(b) Preparation of Plating Media Containing Chromogenic Compounds (I)

Difco Tryptic Soy Agar (TSA) was used as the basal plating medium. TSA was prepared according to manufacturers' instructions. Boiling the medium melted the agar in order to portion the medium. The following chemicals in the specified concentrations were added to the hot medium:

Manganese chloride tetrahydrate (Sigma M-3634) at 0.1% (wt/vol).

Tween® 80 (Polyoxyethylene sorbitan monooleate; Difco) at 0.05% (wt/vol).

Sorbitol (Difco 0179) at 20% (wt/vol).

Cupric sulfate pentahydrate (Sigma C-7631) at 0.078 g/100 ml.

Zinc sulfate heptahydrate (Sigma Z-4750) at 0.015 g/100 ml.

Calcium chloride dihydrate (Fisher) at 0.074 g/100 ml.

Magnesium sulfate anhydrous (Sigma M-7506) at 0.012 g/100 ml.

TSA media containing the above chemicals in various combinations were autoclaved at 121° C. for 15 minutes. After autoclaving the media were placed in a water bath set at a temperature of 50° C.

Bovine serum albumin (BSA; Serologicals 82–067) and X-phos-choline (X-CP) or Y-phos-choline (Y-CP) were dissolved in deionized water. The solution was sterilized by filtration through a 0.45 $\mu$m filter. An appropriate volume of the filtrate was added under aseptic conditions to the TSA media that were previously cooled to 50° C.

Final concentration of the BSA was 320 mg/100 ml. Final concentration of X-phos-choline (X-CP) or Y-phos-choline (Y-CP), respectively, was 32 mg/100 ml. The complete TSA media were poured into Petri plates and allowed to solidify. The plates were held at room temperature overnight in the dark to surface dry the media.

Example 8

Inoculation of TSA Media—Testing Efficacy of X-CP and Y-CP

Cells from the 24-hour BHIB cultures mentioned above were streaked on the TSA media containing the specified chemicals. The plates inoculated with *Bacillus cereus, Bacillus thuringiensis* and *Pseudomonas aeruginosa* were incubated aerobically at 35° C. for 24 hours. After incubation, the colonial morphologies were determined with special emphasis on coloration.

Results: Colonial morphologies including coloration for *Bacillus cereus, Bacillus thuringiensis* and *Pseudomonas aeruginosa* on the various TSA media are presented in Table 5.

TABLE 5

| Test Variables TSA + Additives: | Bacillus cereus | Bacillus thuringiensis | Pseudomonas aeruginosa |
|---|---|---|---|
| No additive | White | White | Off white |
| X-CP + BSA | Light to medium Turquoise color | White | Off white |
| X-CP + BSA + cupric sulfate | Faint Turquoise color | White | Off white |
| X-CP + BSA + sorbitol | Very faint Turquoise color | White | Off white |
| X-CP + BSA + Tween ® 80 | Dark Turquoise color | White | Light Turquoise |
| X-CP + BSA + Tween ® 80 + magnesium sulfate | Medium to dark Turquoise color | White | Light to medium Turquoise |
| X-CP + BSA + Tween ® 80 + calcium chloride | Medium Turquoise color | White | Yellowish Turquoise |
| X-CP + BSA + Tween ® 80 + zinc sulfate | Medium Turquoise color | White | Medium to dark Turquoise |
| X-CP + BSA + Tween ® 80 + manganese chloride | Dark intense Blue color | Medium Turquoise color | Yellowish Turquoise |

Colonial morphologies, including coloration, for *Bacillus cereus, Bacillus thuringiensis* and *Pseudomonas aeruginosa* on the various TSA media with a substrate comprising Y-CP are presented in Table 6.

TABLE 6

| Test Variables TSA + Additives: | Bacillus cereus | Bacillus thuringiensis | Pseudomonas aeruginosa |
|---|---|---|---|
| No Additive | White | White | Off white |
| Y-CP + BSA | Faint Turquoise color | White | Off white |
| Y-CP + BSA + cupric sulfate | White | White | Off white |
| Y-CP + BSA + sorbitol | White | White | Off white |
| Y-CP + BSA + Tween ® 80 | Medium Turquoise color | White | Very light Turquoise |
| Y-CP + BSA + Tween ® 80 + magnesium sulfate | Medium Turquoise color | White | Light Turquoise |
| Y-CP + BSA + Tween ® 80 + calcium chloride | Faint Turquoise color | White | Yellowish very light Turquoise |
| Y-CP + BSA + Tween ® 80 + zinc sulfate | Light Turquoise color | White | Medium Turquoise |
| Y-CP + BSA + Tween ® 80 + manganese chloride | Dark Blue color | Medium Turquoise color | Yellowish Turquoise |

As can be seen from Tables 5 and 6, the nonionic detergent and surfactant, respectively, Tween® 80 caused an enhancement of the expression of the PC-PLC enzyme as indicated by the turquoise to blue colony color for *Bacillus cereus*. Further addition of manganese chloride led to a turquoise color for the *Bacillus thuringiensis* colonies, whereas zinc sulfate caused an increase of the expression of PC-PLC for *Pseudomonas aeruginosa* as indicated by medium to dark turquoise colony color.

The data in Tables 5 and 6 indicate clearly that use of the chromogenic compounds X-phos-choline (X-CP) and Y-phos-choline (Y-CP) permit detection of PC-PLC by formation of a turquoise-to-blue colony color. The two compounds and substrates, respectively, behave quite similarly. However, color intensity with Y-CP is slightly reduced. These data also indicate that PC-PLC expression by the tested bacteria is influenced by the particular additive or combination, and their concentrations, added to the plating medium.

It should be noted that while the above examples are concerned with 3-Indoxyl choline phosphate and with X-phos-choline—preferred compounds of formula (I)—it is apparent from the above disclosure that similar results will be obtained with other substrates of formula (I) if substituents $R^1$, $R^2$, $R^3$, $R^4$ of the benzene nucleus of formula (I) compounds are selected by persons experienced in the art in a manner known, per se, from the chemistry of indigo-type dyes and in histochemistry.

As outlined above, PC-PLCs are produced by a variety of human pathogens and the invention can be applied in various ways, e.g. by screening for bacterial enzyme production directly on plating media, e.g. of clinical samples or cultures isolated from food.

Generally, the invention provides for safe and sensitive detection of potentially pathogenic bacterial activity of such microbes as *Clostridium perfringens, Bacillus cereus, Bacillus anthracis, Pseudomonas aeruginosa, Listeria monocytogenes, Helicobacter pylori, Legionella pneumophila* and others in materials which may contain such activity. Typical examples of such materials include physiological samples, such as blood, urine, faeces, and lymph, as well as goods for consumption, such as food or beverages, and any other potentially infected objects or articles including garments, carpets, household textiles, furniture, vehicles for private or public use, kitchen utensils or kitchen installations for private and commercial use as well as air circulating apparatus and other means in contact with the public, such as mail sorting and delivering devices.

While some preferred embodiments of the invention have been specifically described herein, it will be apparent to those skilled in the art that variations and modifications of the various embodiments shown and described herein may be made without departing from the spirit and scope of the invention. Accordingly, it is intended that the invention be limited only to the extent required by the appended claims and the applicable rules of law.

Accordingly, what is claimed is:

1. A chromogenic 3-indoxyl choline phosphate compound of formula (I):

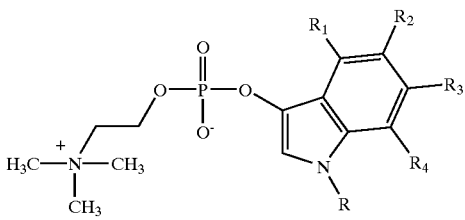

(I)

wherein R is selected from the group consisting of hydrogen and $C_{1-4}$ alkyl while $R^1$, $R^2$, $R^3$, and $R^4$ are independently selected from the group consisting of hydrogen, halogen, cyano, nitro, carboxy, sulphonyl, amino, aminomethyl, hydroxy, $C_{1-4}$ alkoxy, carboxyalkyl in which the alkyl group is a $C_{1-4}$ alkyl group, and an amino group substituted with at least one but not more than two $C_{1-4}$ alkyl groups.

2. The compound of claim 1, wherein R is selected from the group consisting of hydrogen and methyl; $R^1$ is selected from the group consisting of hydrogen and halogen; $R^2$ is selected from the group consisting of hydrogen, halogen, cyano, and nitro; and $R^3$ and $R^4$ are independently selected from the group consisting of hydrogen and halogen.

3. The compound of claim 2, wherein R is hydrogen, $R^1$ is selected from the group consisting of hydrogen and chlorine, $R^2$ is selected from the group consisting of hydrogen and bromine, $R^3$ is selected from the group consisting of hydrogen, chlorine and fluorine, and $R^4$ is hydrogen.

4. The compound of claim 2, wherein R, $R^1$ and $R^4$ each represent hydrogen, $R^2$ is selected from the group consisting of hydrogen and bromine, and $R^3$ is chlorine.

5. 5-Bromo-4-chloro-3-indoxyl choline phosphate represented by formula (IV):

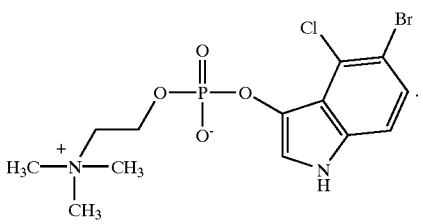

(IV)

6. 3-Indoxyl choline phosphate represented by formula (V):

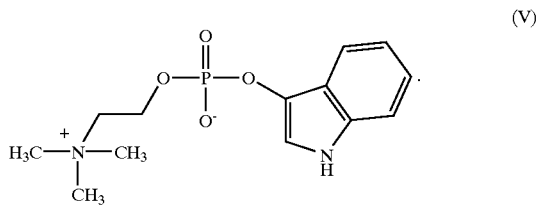

(V)

7. A substrate for detecting a phosphatidylcholine-specific phospholipase C enzyme as an indication of microbial activity; said substrate comprising at least one chromogenic 3-indoxyl choline phosphate compound as defined in claim 1.

8. The substrate of claim 7 wherein said compound is as defined in claim 2.

9. The substrate of claim 7 wherein said compound is as defined in claim 3.

10. The substrate of claim 7 wherein said compound is as defined in claim 4.

11. The substrate of claim 7 wherein said compound is as defined in claim 5.

12. The substrate of claim 7 wherein said compound is as defined in claim 6.

13. The substrate of claim 7 additionally comprising at least one additive selected from the group consisting of serum albumin, surfactants and metal ions.

14. The substrate of claim 13, wherein said metal ion is a divalent ion of metal selected from the group consisting of cobalt, manganese, nickel, zinc, calcium and magnesium.

15. A method of detecting a phosphatidylcholine-specific phospholipase-C enzyme comprising the steps of:
contacting a sample suspected of containing said phosphatidylcholine-specific phos-pholipase-C enzyme with a substrate containing at least one 3-indoxyl choline phosphate compound of formula (I):

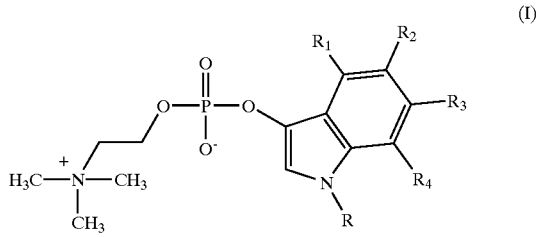

(I)

wherein R is selected from the group consisting of hydrogen and $C_{1-4}$ alkyl while $R^1$, $R^2$, $R^3$, and $R^4$ are independently selected from the group consisting of hydrogen, halogen, cyano, nitro, carboxy, amino, aminomethyl, hydroxy, $C_{1-4}$ alkoxy, carboxyalkyl in which the alkyl group is a $C_{1-4}$ alkyl group, sulphonyl, and amino substituted with at least one but not more than two $C_{1-4}$ alkyl groups, said compound of formula (I) being susceptible to cleavage by said enzyme yielding a dye; and monitoring for color formation as a consequence of said sample suspected of said phosphatidylcholine-specific phospholipase-C enzyme.

16. The method of claim 15 wherein R is selected from the group consisting of hydrogen and methyl; $R^1$ is selected from the group consisting of hydrogen and halogen; $R^2$ is selected from the group consisting of hydrogen, halogen, cyano, nitro; and $R^3$ and $R^4$ are independently selected from the group consisting of hydrogen and halogen.

17. The method of claim 15, wherein R is hydrogen, $R^1$ is selected from the group consisting of hydrogen and chlorine, $R^2$ is selected from the group consisting of hydrogen and bromine, $R^3$ is selected from the group consisting of hydrogen, chlorine and fluorine, and $R^4$ is hydrogen.

18. The method of claim 15, wherein said at least one compound is 5-bromo-4-chloro-3-indoxyl choline phosphate represented by formula (IV):

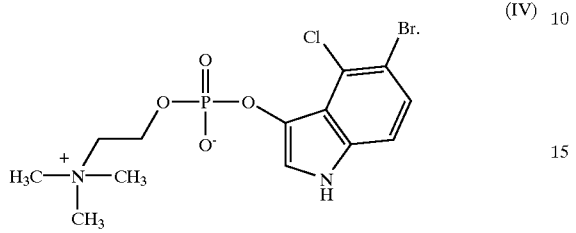
(IV)

19. The method of claim 15, wherein said at least one compound is 3-indoxyl choline phosphate represented by formula (V):

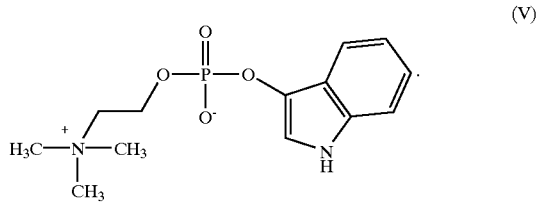
(V)

20. The method of claim 15, wherein said substrate further comprises at least one additive selected from the group consisting of serum albumin, surfactants and metal ions.

21. The method of claim 20, wherein said metal ion is a divalent ion of a metal selected from the group consisting of cobalt, manganese, nickel, zinc, calcium and magnesium.

22. The method of claim 15, wherein said phosphatidylcholine-specific phospholipase-C enzyme derives from a pathogen selected from the group consisting of *Clostridium perfringens, Clostridium novyi, Bacillus cereus, Bacillus thuringiensis, Bacillus anthracis, Pseudomonas aeruginosa, Helicobacter pylori, Legionella pneumophila, Listeria monocytogenes, Aspergillus fumigatus,* and *Candida albicans.*

23. The method of claim 18, wherein said phosphatidylcholine-specific phospholipase-C enzyme derives from a pathogen selected from the group consisting of *Clostridium perfringens, Clostridium novyi, Bacillus cereus, Bacillus thuringiensis, Bacillus anthracis, Pseudomonas aeruginosa, Helicobacter pylori, Legionella pneumophila, Listeria monocytogenes, Aspergillus fumigatus,* and *Candida albicans.*

24. The method of claim 19, wherein said phosphatidylcholine-specific phospholipase-C enzyme derives from a pathogen selected from the group consisting of *Clostridium perfringens, Clostridium novyi, Bacillus cereus, Bacillus thuringiensis, Bacillus anthracis, Pseudomonas aeruginosa, Helicobacter pylori, Legionella pneumophila, Listeria monocytogenes, Aspergillus fumigatus,* and *Candida albicans.*

25. A method of detecting microbial activity in a sample; said method comprising the steps of (i) combining said sample with a substrate comprising at least one compound of formula (I) as defined in claim 1; and (ii) inspecting said sample combined with said substrate by colorimetric means.

26. The method of claim 25 wherein said substrate further comprises at least one additive selected from the group consisting of serum albumin, surfactants and metal ions.

27. The method of claim 26, wherein said metal ion is a divalent ion of a metal selected from the group consisting of cobalt, manganese, nickel, zinc, calcium or magnesium.

28. The method of claim 26 when performed as a screening test in the detection of bacteria of the group including *Clostridium perfringens, Clostridium novyi, Bacillus cereus, Bacillus thuringiensis, Bacillus anthracis, Pseudomonas aeruginosa, Helicobacter pylori, Legionella pneumophila* and *Listeria monocytogenes* as well as in the detection of the yeast *Candida albicans.*

29. The method of claim 27 when performed as a screening test in the detection of bacteria of the group including *Clostridium perfringens, Clostridium novyi, Bacillus cereus, Bacillus thuringiensis, Bacillus anthracis, Pseudomonas aeruginosa, Helicobacter pylori, Legionella pneumophila* and *Listeria monocytogenes* as well as in the detection of the yeast *Candida albicans.*

30. A kit for detecting a phosphatidylcholine-specific phospholipase-C enzyme as an indication of microbial activity; said kit including at least one compound of formula (I) as defined in claim 1.

31. An assay method for detection of PC-PLC by means of a substrate as defined in claim 7.

32. An assay method for detection of the presence of pathogenic strains of *Clostridium perfringens* in a sample suspected to contain such strains by means of a substrate as defined in claim 7.

33. An assay method for detection of the presence of pathogenic strains of *Clostridium perfringens, Bacillus cereus, Bacillus anthracis* or *Bacillus thuringiensis* in a sample suspected to contain such strains by means of a substrate comprising 5-bromo-4-chloro-3-in doxyl choline phosphate represented by formula (IV)

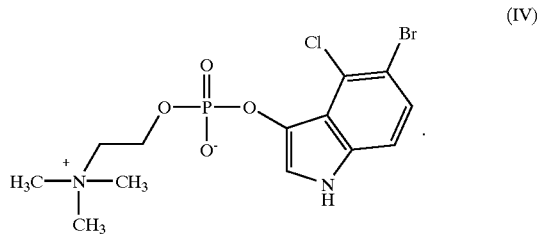
(IV)

34. An assay method for detecting the presence of pathogenic strains of *Clostridium perfringens Bacillus cereus, Bacillus anthracis* or *Bacillus thuringiensis* in a sample suspected to contain such strains by means of a substrate comprising 3-indoxyl choline phosphate represented by formula (V)

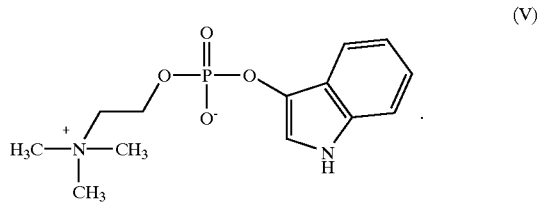
(V)

35. An assay method for detecting the presence of pathogenic strains of *Clostridium perfringens* in a sample suspected to contain such strains by means of a substrate comprising 5-bromo-4-chloro-3-indoxyl choline phosphate represented by formula (IV) or 3-indoxyl choline phosphate represented by formula (V), bovine serum albumin and at least one source of $Co^{2+}$ ions.

36. An assay method for detecting the presence of pathogenic strains of *Bacillus cereus, Bacillus anthracis* or *Bacillus thuringiensis* in a sample suspected to contain such strains by means of a substrate comprising a compound selected from the group consisting of 5-bromo-4-chloro-3-indoxyl choline phosphate and 3-indoxyl choline phosphate, bovine serum albumin, polyoxyethylene sorbitan monooleate and at least one source of $Mn^{2+}$ ions.

37. An assay method for detecting the presence of pathogenic strains of *Pseudomonas aeruginosa* in a sample suspected to contain such strains by means of a substrate comprising at least one compound selected from the group consisting of 5-bromo-4-chloro-3-indoxyl choline phosphate and 3-indoxyl choline phosphate, bovine serum albumin, polyoxyethylene sorbitan monooleate and at least one source of $Zn^{2+}$ ions.

38. A method of identifying a bacterial microorganism of interest, which is capable of producing a phosphatidylcholine-specific phospholipase-C (PC-PLC) enzyme comprising the steps of:

(A) providing a test sample suspected of containing said microorganism of interest;
(B) submitting said test sample to an enrichment broth step if required;
(C) transferring a portion, at least, of said test sample or the product obtained in step (B) to a medium suitable for culturing said microorganism; said medium containing at least one compound of formula (I)

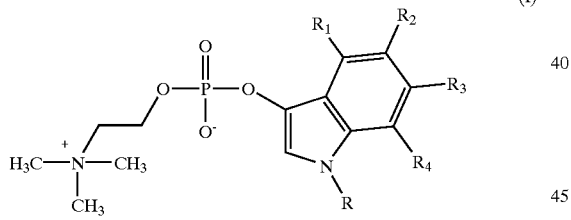

wherein R is selected from the group consisting of hydrogen and $C_{1-4}$ alkyl while $R^1$, $R^2$, $R^3$, and $R^4$ are independently selected from the group consisting of hydrogen, halogen, cyano, nitro, carboxy, amino, aminomethyl, hydroxy, $C_{1-4}$ alkoxy, carboxyalkyl in which the alkyl group contains from 1 to 4 carbon atoms, sulphonyl, and amino substituted with at least one but not more than two $C_{1-4}$ alkyl groups, said compound being capable of producing a color when exposed to said microorganism;

(D) cultivating said medium with said transferred portion for developing at least one colony exhibiting said color; and
(E) recovering a portion, at least, of said colored colony for final identification.

39. A method of preparing a chromogenic 3-indoxyl choline phosphate compound of formula (I):

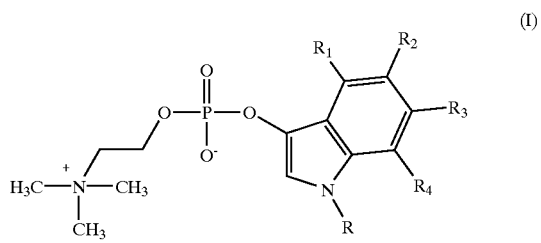

wherein R is selected from the group consisting of hydrogen and $C_{1-4}$ alkyl while $R^1$, $R^2$, $R^3$, and $R^4$ are independently selected from the group consisting of hydrogen, halogen, cyano, nitro, carboxy, amino, aminomethyl, hydroxy, $C_{1-4}$ alkoxy, carboxyalkyl in which the alkyl group contains from 1 to 4 carbon atoms, sulphonyl, and amino substituted with at least one but not more than two $C_{1-4}$ alkyl groups;

comprising the steps of reacting a corresponding indoxyl-3-dichlorophosphate of formula (II) with a salt of choline in order to obtain an intermediate compound (III) according to the reaction:

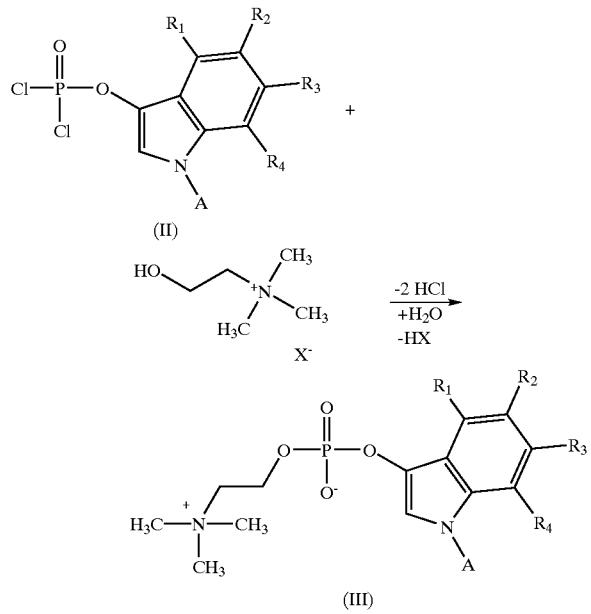

in which A is selected from the group consisting of hydrogen, $C_{1-4}$ alkyl, and an N-protecting group while X is a counter anion of said salt of choline; and removing said N-protecting group from said intermediate of formula (III) when A represents said N-protecting group and, if necessary for obtaining said formula (I) compound, introducing said group R into said intermediate of formula (III).

40. A method of preparing a substrate capable of detecting a microbial phosphatidylcho-line-specific phospholipase-C enzyme wherein said method comprises producing said substrate by incorporating therein a 3-indoxyl choline phosphate compound of formula (I):

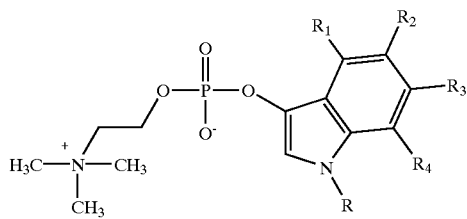 (I)

wherein R is selected from the group consisting of hydrogen and $C_{1-4}$ alkyl while $R^1$, $R^2$, $R^3$, and $R^4$ are independently selected from the group consisting of hydrogen, halogen, cyano, nitro, carboxy, amino, aminomethyl, hydroxy, $C_{1-4}$ alkoxy, carboxyalkyl in which the alkyl moiety contains from one to four carbon atoms, sulphonyl, and amino substituted by at least one but not more than two $C_{1-4}$ alkyl groups.

* * * * *

UNITED STATES PATENT AND TRADEMARK OFFICE
CERTIFICATE OF CORRECTION

PATENT NO. : 6,660,494 B2
DATED : December 9, 2003
INVENTOR(S) : Günter Schabert, Lawrence Restaino and Elon W. Frampton It is certified that error appears in the above-identified patent and that said Letters Patent is hereby corrected as shown below:

Title page,
Item [57], ABSTRACT, after Formula I, line 9, change "calorimetrically" to
-- colorimetrically --.

Column 3,
Line 28, change "calorimetrically" to -- colorimetrically --.

Column 4,
Line 56, change "developping" to -- developing --.

Column 8,
Line 36, change "calorimetric" to -- colorimetric --.

Column 22,
Line 34, change "5-bromo-4-chloro-3-in doxyl" to -- 5-bromo-4-chloro-3-indoxyl --.

Signed and Sealed this

Fourth Day of May, 2004

JON W. DUDAS
*Acting Director of the United States Patent and Trademark Office*